US008927580B2

(12) United States Patent
Richardson et al.

(10) Patent No.: US 8,927,580 B2
(45) Date of Patent: Jan. 6, 2015

(54) THIOSEMICARBAZONE COMPOUNDS AND USE IN THE TREATMENT OF CANCER

(75) Inventors: Des R. Richardson, Sydney (AU); David B. Lovejoy, Redfern (AU)

(73) Assignee: Oncochel Therapeutics LLC, Sausalito, CA (US)

( * ) Notice: Subject to any disclaimer, the term of this patent is extended or adjusted under 35 U.S.C. 154(b) by 0 days.

(21) Appl. No.: 13/994,355

(22) PCT Filed: Dec. 16, 2011

(86) PCT No.: PCT/AU2011/001631
§ 371 (c)(1),
(2), (4) Date: Aug. 20, 2013

(87) PCT Pub. No.: WO2012/079128
PCT Pub. Date: Jun. 21, 2012

(65) Prior Publication Data
US 2014/0206725 A1 Jul. 24, 2014

(30) Foreign Application Priority Data
Dec. 17, 2010 (AU) .............................. 2010905539

(51) Int. Cl.
*A61K 31/435* (2006.01)
*C07D 213/53* (2006.01)

(52) U.S. Cl.
CPC ............ *C07D 213/53* (2013.01); *A61K 31/435* (2013.01)
USPC ......................................... 514/332; 546/265

(58) Field of Classification Search
CPC ............................ A61K 31/435; C07D 213/53
USPC ......................................... 514/332; 546/265
See application file for complete search history.

(56) References Cited

FOREIGN PATENT DOCUMENTS

| CN | 1891701 A | 1/2007 |
|---|---|---|
| DE | 42 07 400 A1 | 9/1993 |
| WO | 2004/069801 A1 | 8/2004 |
| WO | 2012/079128 A1 | 6/2012 |

OTHER PUBLICATIONS

PCT International Preliminary Report on Patentability of PCT International Application No. PCT/AU2011/001631, dated Jun. 18, 2013.
PCT International Search Report of PCT International Application No. PCT/AU2011/001631, dated Feb. 21, 2012.
Kovacevic et al., "Iron Chelators: Development of Novel Compounds with High and Selective Anti-Tumour Activity," Current Drug Delivery 7(3):194-207 (2010).
Richardson et al., "Cancer cell iron metabolism and the development of potent iron chelators as anti-tumour agents," Biochimica et Biophysica Acta 1790(7):702-717 (2009).
Whitnall et al., "A class of iron chelators with a wide spectrum of potent antitumor activity that overcomes resistance to chemotherapeutics," Proc. Nat'l Acad. Sci. USA 103(40):14901-14906 (2006).
March, Advanced Organic Chemistry, 4th Ed (John Wiley & Sons, New York, 1992).
Attia et al., "A phase 2 consortium (P2C) trial of 3-aminopyridine-2-carboxaldehyde thiosemicarbazone (3-AP) for advanced adenocarcinoma of the pancreas," Invest New Drugs 26:369-379 (2008).
Baker et al., "Evaluation of the Iron Chelation Potential of Hydrazones of Pyridoxal, Salicylaldehyde and 2-Hydroxy-1-Naphthylaldehyde using the Hepatocyte in Culture," Hepatology 15(3):492-501 (1992).
Balsari et al., "Combination of CpG-oligodeoxynucleotide and a topoisomerase I inhibitor in the therapy of human tumour xenografts," Eur. J. Cancer 40:1275-1281 (2004).
Berge et al., "Pharmaceutical Salts," J. Pharmaceutical Sciences 66(1):1-19 (1977).
Dunn et al., "The function of melanotransferrin: a role in melanoma cell proliferation and tumorigenesis," Carcinogenesis 27(11):2157-2169 (2006).
Gao et al., "The potential of iron chelators of the pyridoxal isonicotinoyl hydrazone class as effective antiproliferative agents, IV: the mechanisms involved in inhibiting cell-cycle progression," Blood 98(3):842-50 (2001).
Kalinowski et al., "Design, Synthesis, and Characterization of Novel Iron Chelators: Structure-Activity Relationships of the 2-Benzoylpyridine Thiosemicarbazone Series and Their 3-Nitrobenzoyl Analogues as Potent Antitumor Agents," J. Med. Chem. 50(15):3716-3729 (2007).
Kovacevic et al., "The metastasis suppressor, Ndrg-1: a new ally in the fight against cancer," Carcinogenesis 27 (12):2355-2366 (2006).
Liu et al., "Synthesis and Antitumor Activity of Amino Derivatives of Pyridine-2-carboxaldehyde Thiosemicarbazone," J. Med. Chem. 35(20):3672-3677 (1992).
Ma et al., "A multicenter phase II trial of 3-aminopyridine-2-carboxaldehyde thiosemicarbazone (3-AP, Triapine®) and gemcitabine in advanced non-small-cell lung cancer with pharmacokinetic evaluation using peripheral blood mononuclear cells," Invest New Drugs 26:169-73 (2008).

(Continued)

*Primary Examiner* — Raymond Henley, III
(74) *Attorney, Agent, or Firm* — Sam L. Nguyen; Hamilton DeSanctis & Cha, LLP

(57) ABSTRACT

The present invention relates to dipyridyl thiosemicarbazone compounds of formula (I): wherein $R^1$ is cyclohexyl or ethyl; as well as pharmaceutical compositions containing those compounds, and the use of those compounds and compositions in the treatment of cancer.

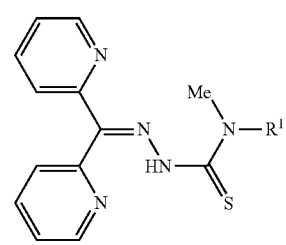

13 Claims, 14 Drawing Sheets

(56) References Cited

OTHER PUBLICATIONS

Maruyama et al., "Tumor Growth Suppression in Pancreatic Cancer by a Putative Metastasis Suppressor Gene Cap43/NDRG1/Drg-1 through Modulation of Angiogenesis," Cancer Research 66(12):6233-42 (2006).

Merck Index, An Encyclopaedia of Chemicals, Drugs, and Biologicals, 12th Ed. (1996).

Handbook of Pharmaceutical Salts: Properties, Selection, and Use (Stahl and Wermuth eds., Wiley-VCH, Weinheim, Germany (2002).

Remington's Pharmaceutical Sciences, 19th Edition (Mack Publishing Company, 1995).

Richardson et al., "Dipyridyl Thiosemicarbazone Chelators with Potent and Selective Antitumor Activity Form Iron Complexes with Redox Activity," J. Med. Chem. 49(22):6510-6521 (2006).

Richardson et al., "The potential of iron chelators of the pyridoxal isonicotinoyl hydrazone class as effective antiproliferative agents," Blood 86(11):4295-4306 (1995).

Scovill, JP, "A Facile Synthesis of Thiosemicarbazides and Thiosemicarbazones by the Transamination of 4-Methyl-4-phenyl-3-thiosemicarbazine," Phosphorous, Sulphur, and Silicon 60:15-19 (1990).

Vogel's Textbook of Practical Organic Chemistry, 5th Ed (John Wiley & Sons, New York, 1989).

Winterbourn et al., "Oxidation of Human Haemoglobin by Copper: Mechanism and Suggested Role of the Thiol Group of Residue β-93," Biochem. J. 165:141-148 (1977).

A

Dp4e4mT

Dp4cycH4mT

B

Controls

Dp4e4mT-HCl
1.5 mg

Dp4e4mT-HCl
4 mg

Dp4e4mT-HCl
6 mg

Dp44mT
0.75 mg

THIOSEMICARBAZONE COMPOUNDS AND USE IN THE TREATMENT OF CANCER

This application claims priority from Australian Provisional Patent Application No 2010905539 filed 17 Dec. 2010, the entire contents of which are hereby incorporated by cross-reference.

TECHNICAL FIELD

The present invention relates to thiosemicarbazone compounds and their use in therapy. More particularly, the invention relates to a selection of dipyridyl thiosemicarbazone compounds, pharmaceutical compositions containing those compounds, and the use of those compounds and compositions in the treatment of cancer.

BACKGROUND ART

Thiosemicarbazone iron chelators are a class of anti-cancer agents that have been found to be extremely potent and selective against a number of different neoplasms both in vitro and in vivo. These compounds function by targeting iron, an essential element for DNA synthesis, in cancer cells. Iron chelators were initially developed for iron-overload diseases such as β-thalassemia, with the chelator desferrioxamine (DFO) being the most widely used treatment for this disease. However, clinical trials examining DFO against neuroblastoma found that this agent was effective at inhibiting the progression of this cancer in some patients. These early studies were the first to identify the potential of iron chelators as anti-cancer agents. Since then, iron chelators designed specifically for the treatment of cancer have been developed, with the thiosemicarbazone iron chelator 3-aminopyridine-2-carboxaldehyde thiosemicarbazone (Triapine®) (Vion Pharmaceuticals, New Haven Conn., United States of America) entering a number of phase I and II clinical trials.

Thiosemicarbazone iron chelators function by binding iron and copper and forming redox-active complexes, leading to the production of reactive oxygen species (ROS) that induce cancer cell cytotoxicity. One of the most active compounds developed to date is a thiosemicarbazone class of iron chelator, di-2-pyridylketone 4,4-dimethyl-3-thiosemicarbazone, (abbreviated herein as Dp44mT), which is described in WO 2004/069801. Dp44mT has been demonstrated to markedly and significantly reduce the growth of a number of different tumors in vitro and in vivo and was found to be more potent and less toxic than Triapine®. However, studies using high, non-optimal doses of Dp44mT found that it induced some cardiotoxicity in nude mice.

Thiosemicarbazone compounds target the metastasis suppressor, NDRG1. NDRG1 inhibits both growth and metastasis as well as angiogenesis of pancreatic cancer in vivo leading to reduced tumor progression. Moreover, NDRG1 has also recently been correlated with increased differentiation of pancreatic cancers and its potential as a promising therapeutic target against pancreatic cancer has been reported (eg, Kovacevic, Z. and D. R. Richardson (2006). *Carcinogenesis* 27: 2355-66; Maruyama, Y., M. Ono, et al. (2006). *Cancer Res* 66: 6233-42). NDRG1 has a number of key molecular targets in pancreatic cancer including the tumor suppressors PTEN and SMAD4, both of which are up-regulated in response to NDRG1. Therefore, NDRG1 may be a promising therapeutic target, especially for the treatment of pancreatic cancer. NDRG1 was recently found to be up-regulated using iron-chelating anti-cancer agents in vitro and in vivo. Iron chelators increased NDRG1 expression via hypoxia-inducible transcription factor (HIF-1)-dependent mechanisms, although HIF-1-independent pathways have also been observed. Iron-chelating anti-cancer agents therefore provide an important opportunity to target NDRG1 expression in cancer cells by cellular iron depletion.

There is a need for new and alternative treatments for cancer. The present invention is directed to a selection of thiosemicarbazone compounds that advantageously inhibit cellular proliferation and may be useful for the treatment of cancer.

SUMMARY OF INVENTION

In one aspect, the present invention relates to thiosemicarbazone compounds of general formula (I):

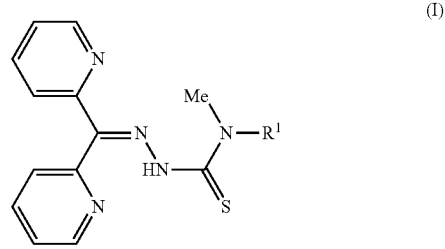

(I)

wherein $R^1$ is cyclohexyl or ethyl;
and salts, hydrates and solvates thereof.

In a preferred embodiment the invention relates to the compound di-2-pyridylketone 4-ethyl-4-methyl-3-thiosemicarbazone (abbreviated herein as Dp4e4mT) and salts, hydrates and solvates thereof.

In another preferred embodiment the invention relates to the compound di-2-pyridylketone 4-cyclohexyl-4-methyl-3-thiosemicarbazone (abbreviated herein as Dp4cycH4mT), salts, hydrates and solvates thereof.

In preferred embodiments the salts are pharmaceutically acceptable salts. Acid addition salts, such as hydrochloride salts, are a particularly preferred embodiment of the invention.

In another aspect the invention relates to a pharmaceutical composition comprising a compound of formula (I), or a salt, hydrate or solvate thereof, together with a pharmaceutically acceptable excipient, diluent or adjuvant.

In a further aspect the present invention relates to a method of treating cancer in a mammal, the method comprising administering to a mammal in need thereof an effective amount of a compound of formula (I) or a salt, hydrate or solvate thereof, or a pharmaceutical composition thereof. In preferred embodiments the mammal is a human.

In another aspect the present invention relates to the use of a compound of formula (I) or a salt, hydrate or solvate thereof in the manufacture of a medicament for the treatment of cancer.

In a further embodiment the invention relates to a compound of formula (I) or a salt, hydrate or solvate thereof, or a pharmaceutical composition thereof, for the treatment of cancer.

The compounds of the invention are useful for the treatment of a wide variety of cancers, including solid and non-solid tumours, including but not limited to, melanoma, skin cancer, breast cancer, prostate cancer, bladder cancer, liver cancer, gastrointestinal cancer, colon and rectal cancer, brain tumour, head and neck cancer, bone cancer, pancreatic cancer, uterine cancer, ovarian cancer, cervical cancer, lung cancer as well as haematological tumours (eg, leukaemias and lymphomas). In preferred embodiments the cancer is selected from pancreatic cancer, lung cancer, and brain tumours. In particularly preferred embodiments the cancer is pancreatic cancer. In other particularly preferred embodiments the cancer is lung cancer. In other preferred embodiments the cancer is brain tumour. In preferred embodiments the compounds of the invention are useful for the treatment of solid tumours. In other preferred embodiments the compounds of the invention are useful for the treatment of non-solid tumours.

Other embodiments of the invention disclosed herein are directed to a method of inhibiting cellular proliferation, the method comprising contacting one or more cells with an effective amount of a compound of formula (I) or a salt, hydrate or solvate thereof. The cells may be in vitro or in vivo. Preferably the cells are mammalian cells.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps. Thus, in the context of this specification, the term 'comprising' means 'including principally, but not necessarily solely'.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention, in Australia or elsewhere, before the priority date of each claim of this specification.

DEFINITIONS

Figure 1:
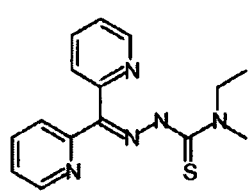
FIG. 1. A Structural formulae of the compounds Dp4e4mT and Dp4cycH4mT. B General synthetic scheme for Dp4cycH4mT FIG. 2. Antiproliferative activity of Dp4e4mT and Dp4cycH4mT against SK-N-MC neuroepithelioma.
Figure 1:
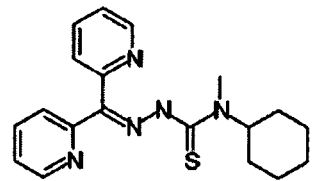
Figure 1:
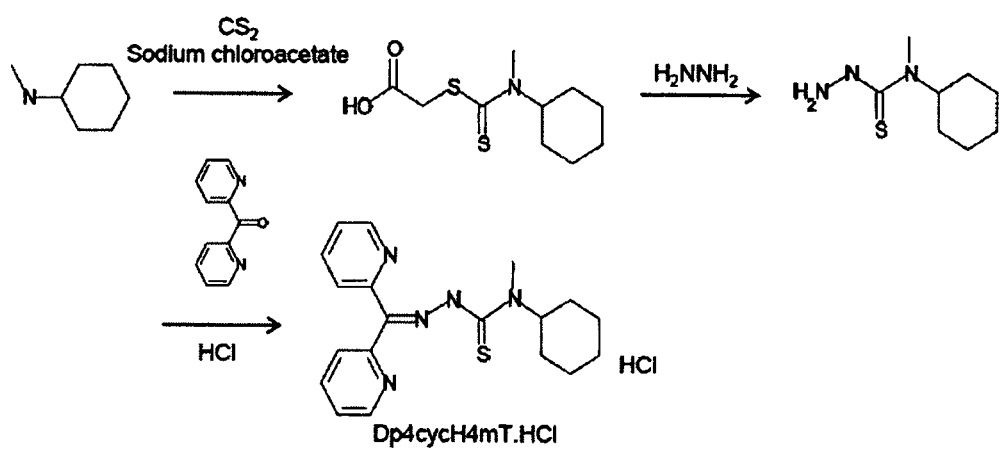

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps, features, compositions and compounds.

The compounds of formula (I) are tridentate ligands capable of chelating transition metal ions, such as iron (Fe(II) and Fe(III)). Accordingly, throughout this specification the compounds of the invention may be referred to as 'ligands', 'chelators' or 'iron chelators'. Throughout this specification, a reference to 'compound(s)' or 'chelators' or 'ligand(s)' of the invention is a reference to compounds of formula (I), including salts, hydrates and solvates thereof, unless expressly indicated otherwise.

The present invention includes within its scope all isomeric forms of the compounds of formula (I) and salts, hydrates and solvates thereof disclosed herein, including all diastereomeric isomers (including cis/trans isomers), racemates and enantiomers.

In the context of this invention the term "administering" and variations of that term including "administer" and "administration", includes contacting, applying, delivering or providing a compound or composition of the invention to an organism, mammal, or a surface by any appropriate means.

In the context of this specification, the term "mammal" includes humans and individuals of any species of social, economic or research importance including but not limited to members of the genus ovine, bovine, equine, porcine, feline, canine, primates (including human and non-human primates), rodents, murine, caprine, leporine, and avian. In preferred embodiments the mammal is a human.

In the context of this specification, the term "treatment", refers to any and all uses which remedy a disease state or symptoms, prevent the establishment of disease, or otherwise prevent, hinder, retard, or reverse the progression of disease or other undesirable symptoms in any way whatsoever. Thus, for the avoidance of doubt, references herein to 'treatment' include references to curative, palliative and prophylactic treatment.

In the context of this specification the term "effective amount" includes within its meaning a sufficient but non-toxic amount of a compound or composition of the invention to provide the desired therapeutic effect. The exact amount required will vary from subject to subject depending on factors such as the species being treated, the age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

DETAILED DESCRIPTION OF EMBODIMENTS OF THE INVENTION

The present invention is directed to a selection of thiosemicarbazone compounds that have antiproliferative properties and which may therefore be useful in the treatment of cancer. In particular, the present invention relates to the thiosemicarbazone compounds of general formula (I):

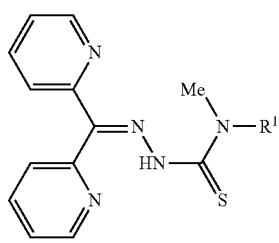
(I)

wherein R¹ is cyclohexyl or ethyl;
and salts, hydrates and solvates thereof.

More particularly, the present invention relates to di-2-pyridylketone 4-ethyl-4-methyl-3-thiosemicarbazone (Dp4e4mT) and di-2-pyridylketone 4-cyclohexyl-4-methyl-3-thiosemicarbazone (Dp4cycH4mT), and to salts, hydrates and solvates thereof:

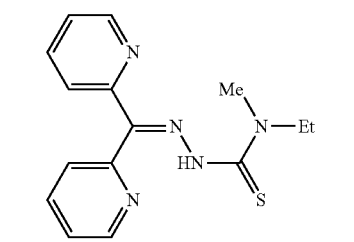
Dp4e4mT

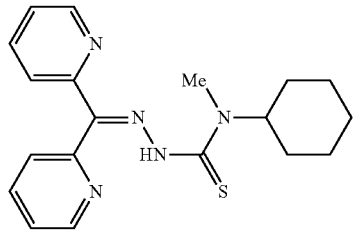
Dp4cycH4mT

Compounds according to the present invention are iron chelators and can chelate Fe(II) and Fe(III). Accordingly, iron complexes (ie, Fe(II) and Fe(III) complexes) of the compounds of formula (I) are also encompassed by the present invention.

Compounds of formula (I) according to the present invention, or salts, hydrates or solvates thereof, may be prepared by methods known to those skilled in the art, including for example, Schiff base condensation of an imine with a ketone, as described for example in *Advanced Organic Chemistry*, 4$^{th}$ Ed (John Wiley & Sons, New York, 1992) and *Vogel's Textbook of Practical Organic Chemistry*, 5$^{th}$ Ed (John Wiley & Sons, New York, 1989).

An exemplary general synthetic scheme for preparing compounds of formula (I) is shown below in Scheme 1:

Scheme 1

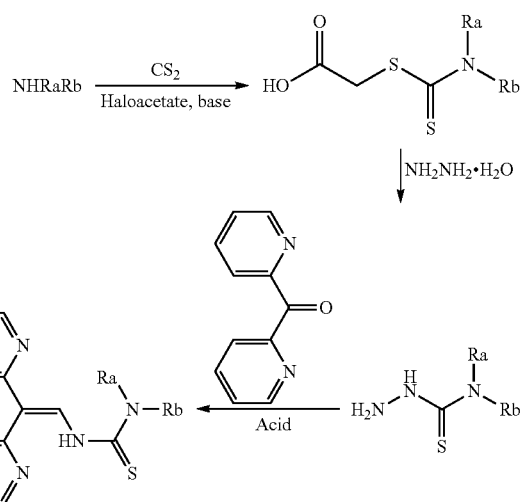

The first step involves the formation of a carboxymethyl dithiocarbamate from the reaction of a secondary amine (NHRaRb) with carbon disulfide. The Ra and Rb groups of the Secondary amine may be the same or different and may be a linear or a cyclic $C_{1-6}$ alkyl. In preferred embodiments of the invention, according to Scheme 1 Ra is methyl and Rb is ethyl or cyclohexyl. Examples of suitable haloacetates include chloroacetate and bromoacetate. Suitable bases will be well known to those skilled in the art and include, for example, sodium hydroxide, potassium hydroxide, lithium hydroxide, ammonia, diethylamine, and the like. Typically, the first step is carried out at ambient temperature eg, about 20-25° C.). Standard acid work-up (eg, with aqueous hydrochloric acid, sulphuric acid, etc) yields the carboxymethyl dithiocarbamate.

The next step involves the formation of a thiosemicarbazide intermediate compound by reacting the carboxymethyl dithiocarbamate with hydrazine hydrate. Typically, this step is carried out in water with gentle heating at a temperature in the range of from about 25° C. to about 60° C. Generally a molar excess of hydrazine hydrate is used.

Next, the thiosemicarbazide compound is reacted in a Schiff-base condensation reaction with di-2-pyridyl ketone to form the thiosemicarbazone compound of formula (I). Typically, this reaction may be carried out in any suitable polar solvent, such as ethanol, propanol, tetrahydrofuran, and the like. The reaction is typically carried out by heating the mixture at reflux for a suitable period of time, which typically may be for about 1 to about 24 hours, for example for about 2 to about 8 hours, more typically for about 2 to about 4 hours. Optionally, water produced during the condensation reaction may be removed by the inclusion of a drying agent, eg $TiCl_4$ or a molecular sieve, or by azeotropic distillation.

Salt forms of the compounds of formula (I) may be readily prepared using techniques known to those skilled in the art. For example, acid addition salts may be prepared by dissolving a compound of formula (I) in a suitable non-polar solvent, such as hexane, dichloromethane, etc, and stirring with an aqueous acid corresponding to the desired salt. For example, hydrochloric acid would yield the hydrochloride salt, nitric acid would yield the nitrate salt, sulfuric acid would yield the sulfate salt, etc.

Compounds of general formula (I) or their salts, hydrates and solvates may be purified using stand techniques known to those skilled in the art. In preferred embodiments, the compounds of formula (I) may be purified by crystallisation from a suitable solvent or mixture of solvents. Suitable solvents would be known to those skilled in the art and include, for example, methanol, ethanol, acetonitrile, ethyl acetate, N,N-dimethylformamide, dimethylsulfoxide, and mixtures thereof. In other embodiments the product may be recrystallised from a solvent mixture comprising one or more organic solvents, such as those listed above, and water. After purification, compounds of general formula (I) may be substantially pure. For example, the compounds of formula (I) may be isolated in a form which is at least about 80%, 85%, 90%, 95%, 98%, or 99% pure.

Therapy

The present invention also relates to the use of thiosemicarbazone compounds of general formula (I) and salts, hydrates and solvates thereof, in therapy. In particular, the thiosemicarbazone compounds of formula (I) have antiproliferative properties and therefore may be useful in the treatment of cancer. The thiosemicarbazone compounds of the present invention are iron chelators. The compounds of the invention may be useful for the treatment of a wide variety of cancers (tumours), including but not limited to, melanoma, skin cancer, breast cancer, prostate cancer, bladder cancer, liver cancer, gastrointestinal cancer, colon and rectal cancer, brain cancer, head and neck cancer, bone cancer, pancreatic cancer, uterine cancer, ovarian cancer, cervical cancer, lung cancer as well as haematological tumours (eg, leukaemias and lymphomas). In particularly preferred embodiments the cancer is pancreatic cancer. In other particularly preferred embodiments the cancer is lung cancer. In other preferred embodiments the cancer is brain cancer. In preferred embodiments the compounds of the invention are useful for the treatment of solid tumours. In other preferred embodiments the compounds of the invention are useful for the treatment of non-solid tumours.

Pancreatic cancer is a devastating disease being fatal in 98-100% of cases within the first 5 years of diagnosis, with the survival from this disease being the same today as it was 20 years ago. The best treatment currently available for pancreatic cancer is the anti-cancer agent, gemcitabine, which is an analogue of the nucleoside, deoxycytidine. Gemcitabine is a prodrug which is converted within the cell to the active metabolites difluorodeoxycytidine di- and triphosphate (dFdCDP, dFdCTP). The success of gemcitabine in pancreatic cancer treatment has been limited. In fact, clinical trials using this agent have found that on average it increases the life-span of patients by only about 3 months. Gemcitabine has been combined with other anticancer agents such as 5-fluorouracil (5-FU) resulting in some improvement of its activity. However, the prognosis for pancreatic cancer patients remains dismal.

Surprisingly, the thiosemicarbazone compounds of the present invention, or salts, hydrates or solvates thereof, advantageously show antiproliferative properties which are at least as good as, and preferably better than, known anticancer agents. For example, in preferred embodiments the thiosemicarbazone compounds of the invention are more effective in inhibiting proliferation of cancer cells (eg, pancreatic cancer cells) when compared to gemcitabine and 5-fluorouracil. The compounds of the present invention (used alone or in combination with other anticancer agents, or as part of a therapeutic regimen), are therefore alternative anticancer agents possessing one or more advantageous therapeutic properties compared to existing anticancer agents.

Another surprising and advantageous feature of the present invention is that the thiosemicarbazone compounds of the present invention, or salts, hydrates or solvates thereof may substantially inhibit pancreatic tumor growth, which is well known to be a particularly aggressive form of cancer. The compounds of the present invention may therefore be used, alone or in combination with other anticancer agents or as part of a therapeutic regimen, in the treatment of pancreatic cancer. In preferred embodiments the thiosemicarbazone compound is Dp4e4mT or a salt or hydrate thereof. In other preferred embodiments the thiosemicarbazone is Dp4cycH4mT or a salt or hydrate thereof.

A further surprising and advantageous feature of the present invention is that the thiosemicarbazone compounds of the present invention may be more effective and less toxic than the potent antiproliferative thiosemicarbazone compound di-2-pyridylketone 4,4-dimethyl-3-thiosemicarbazone (Dp44mT). In particularly preferred embodiments, the thiosemicarbzone compounds of the present invention, eg, Dp4cycH4mT or Dp4e4mT, show substantially less cardiotoxicity than Dp44mT.

The protein myoglobin (Mb) plays an important role in oxygen storage and donation to muscles and is a monomeric counterpart to hemoglobin. In cancer clinical trials involving Triapine®, induction of methemoglobinemia and hypoxia has been noted as a dose-limiting side effect (Attia S, Kolesar J, et al., (2008). *Invest New Drugs* 26: 369-379; Ma B, Goh B C, et al. (2008). *Invest New Drugs* 26: 169-73). In patients that are undergoing chemotherapy for cancer, this complication is undesirable as these patients often have reduced respiratory performance. Accordingly, the excessive production of metHb reduces the clinical utility of Triapine®. The compounds of the present invention, in particular the compound Dp4cycH4mT, possess a further advantage over other anticancer agents because they do not induce methaemoglobin (metHb) and/or metmyoglobin (metMb) formation, or the compounds induce metHb and/or metMb formation to a significantly less extent than other anticancer agents, such as Dp44mT and Triapine®, while maintaining anti-tumor activity.

Formulations

In accordance with the present invention, when used for the treatment or prevention of an infection, disease, or disorder, compound(s) of the invention may be administered alone or in combination with other agents as part of a therapeutic regimen. The compounds may be administered as a pharmaceutical or veterinarial formulation which comprises at least one compound according to the invention. The compound(s) may also be present as suitable salts, including pharmaceutically acceptable salts.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

In other embodiments the compound(s) of the present invention may be formulated in combination with one or more other therapeutic agents.

In other embodiments of the present invention, the compounds of the invention may be included in combination treatment regimens with surgery and/or other known treatments or therapeutic agents, such as other anticancer agents, in particular, chemotherapeutic agents, radiotherapeutic agents, and/or adjuvant or prophylactic agents. Suitable agents are listed, for example, in the Merck Index, *An Encyclopaedia of Chemicals, Drugs and Biologicals,* 12$^{th}$ Ed., 1996, the entire contents of which are incorporated herein by reference.

For example, when used in the treatment of solid tumours, compounds of the present invention may be administered with one or more chemotherapeutic agents or combinations thereof, such as: adriamycin, taxol, docetaxel, fluorouracil, melphalan, cisplatin, alpha interferon, COMP (cyclophosphamide, vincristine, methotrexate and prednisone), etoposide, mBACOD (methotrexate, bleomycin, doxorubicin, cyclophosphamide, vincristine and dexamethasone), PROMACE/MOPP (prednisone, methotrexate (w/leucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM-609, SU-101, CM-101, Techgalan, thalidomide, SP-PG and the like.

Other examples of anticancer agents include alkylating agents such as nitrogen mustards (eg, mechlorethamine, melphalan, chlorambucil, cyclophosphamide, (L-sarcolysin), and ifosfamide), ethylenimines and methylmelamines (eg, hexamethylmelamine, thiotepa), alkylsulfonates (eg, busulfan), nitrosoureas (eg, carmustine, lomustine, semustine, streptozocin), triazenes (eg, dacarbazine (dimethyltriazenoimidazolecarboxamide), temozolomide), folic acid analogues (eg, methotrexate), pyrimidine analogues (eg, 5-fluorouricil, floxuridine, cytarabine, gemcitabine), purine analogues (eg, 6-mercaptopurine, 6-thioguanine, pentostatin (2'-deoxycoformycin) cladribine, fludarabine), vinca alkaloids (eg, vinblastine, vincristine), taxanes (eg, paclitaxel, docetaxel), epipodophyllotoxins (eg, etoposide, teniposide), camptothecins (topotecan, irinotecan), antiobiotics (eg, actinomycin D, daunorubicin (daunomycin, rubidomycin), doxorubicin, bleomycin, mitomycin C, methramycin), enzymes (eg, L-asparaginase), interferon-alpha, interleukin-2, cisplatin, carboplatin, mitoxantrone, hydroxyurea, procarbazine, mitotane, aminoglutethimide, imatinib, adrenocorticosteroids (eg, prednisone), progestins (eg, hydroxyprogesterone caproate, medroxyprogesterone acetate, megestrol acetate), oestrogens (eg, diethylstilbestrol, ethinyl estradiol), antiestrogen (eg, tamoxifen, anastrozole), androgens (eg, testosterone propionate, fluoxymesterone), antiandrogens (eg, flutamide), and gonadotropin-releasing hormone analogues (eg, leuprolide).

In particularly preferred embodiments one more compounds of the invention may be used in combination with gemcitabine or 5-fluorouracil, or in combination with gemcitabine and 5-fluorouracil.

Combination regimens may involve the active agents being administered together, sequentially, or spaced apart as appropriate in each case. Combinations of active agents including compounds of the invention may be synergistic.

By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art. Acid addition salts, such as hydrochloride salts, are a particularly preferred embodiment of the invention.

For example, suitable pharmaceutically acceptable salts of compounds according to the present invention may be prepared by mixing the compounds of the invention with a pharmaceutically acceptable acid (including inorganic and organic acids) or a pharmaceutically acceptable base (including inorganic and organic bases). Suitable pharmaceutically acceptable salts of the compounds of the present invention therefore include acid addition salts and base salts.

Suitable pharmaceutically acceptable acids include but are not limited to acetic acid, benzenesulfonic acid, benzoic acid, camphorsulfonic acid, citric acid, ethenesulfonic acid, fumaric acid, gluconic acid, glutamic acid, hydrobromic acid, hydrochloric acid, isethionic acid, lactic acid, maleic acid, malic acid, malonic acid, mandelic acid, methanesulfonic acid, mucic acid, nitric acid, pamoic acid, pantothenic acid, phosphoric acid, oxalic acid, succinic acid, sulfuric acid, tartaric acid, p-toluenesulfonic acid, and the like. Presently preferred acid addition salts are hydrochloric, hydrobromic, phosphoric, and sulfuric salts, and most particularly preferred is the hydrochloric salt.

Suitable base salts may be formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

S. M. Berge et al. describe pharmaceutically acceptable salts in detail in *J. Pharmaceutical Sciences,* 1977, 66:1-19 and a review on suitable salts is provided by *Handbook of Pharmaceutical Salts: Properties, Selection, and Use* by Stahl and Wermuth (Wiley-VCH, Weinheim, Germany, 2002), both of which are incorporated herein in their entirety.

The salts can be prepared in situ during the final isolation and purification of the compounds of the invention, or separately by reacting the free base compound with a suitable organic acid. Representative acid addition salts include acetate, adipate, alginate, ascorbate, asparate, benzenesulfonate, benzoate, bisulfate, borate, butyrate, camphorate, camphorsulfonate, citrate, digluconate, cyclopentanepropionate, dodecylsulfate, ethanesulfonate, fumarate, glucoheptonate, glycerophosphate, hemisulfate, heptonate, hexanoate, hydrobromide, hydrochloride., hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium potassium, calcium, magnesium, and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like.

Convenient modes of administration of compounds of the invention include parenteral (eg, subcutaneous, intravenous, intramuscular, intradermal, intraperitoneal, intrathecal, intraocular, intranasal, intraventricular injection or infusion techniques), intraperitoneal, oral administration, inhalation, transdermal application, topical creams or gels or powders, or rectal administration. Depending on the route of administration, the formulation and/or compound may be coated with a material to protect the compound from the action of enzymes, acids and other natural conditions which may inactivate the therapeutic activity of the compound.

Dispersions of the compounds according to the invention may also be prepared in glycerol, liquid polyethylene glycols, and mixtures thereof and in oils. Under ordinary conditions of storage and use, pharmaceutical preparations may contain a preservative to prevent the growth of microorganisms.

Pharmaceutical compositions suitable for injection include sterile aqueous solutions (for suitably water soluble active agents) or dispersions and sterile powders for the extemporaneous preparation of sterile injectable solutions or dispersions. Ideally, the composition is stable under the conditions of manufacture and storage and may include a preservative to stabilise the composition against the contaminating action of microorganisms such as bacteria and fungi.

In one embodiment of the invention, the compound(s) of the invention may be administered orally, for example, with an inert diluent or an assimilable edible carrier. The compound(s) and other ingredients may also be enclosed in a hard or soft shell gelatin capsule, compressed into tablets, or incorporated directly into an individual's diet. For oral therapeutic administration, the compound(s) may be incorporated with excipients and used in the form of ingestible tablets, buccal tablets, troches, capsules, elixirs, suspensions, syrups, wafers, and the like. Suitably, such compositions and preparations may contain at least 1% by weight of active compound. The percentage of the compound(s) of the invention in pharmaceutical compositions and preparations may, of course, be varied. For example, the amount may conveniently range from about 2% to about 90%, about 5% to about 80%, about 10% to about 75%, about 15% to about 65%; about 20% to about 60%, about 25% to about 50%, about 30% to about 45%, or about 35% to about 45%, of the weight of the dosage unit. The amount of compound in therapeutically useful compositions is such that a suitable dosage can be obtained. Suitable does may be obtained by single or multiple administrations.

The term "pharmaceutically acceptable carrier" is intended to include solvents, dispersion media, coatings, anti-bacterial and anti-fungal agents, isotonic and absorption delaying agents, and the like. The use of such media and agents for pharmaceutically active substances is well known in the art. Except insofar as any conventional media or agent is incompatible with the compound, use thereof in the therapeutic compositions and methods of treatment and prophylaxis is contemplated. Supplementary active compounds may also be incorporated into the compositions according to the present invention. It is especially advantageous to formulate parenteral compositions in dosage unit form for ease of administration and uniformity of dosage.

The term "dosage unit form" as used herein refers to physically discrete units suited as unitary dosages for the individual to be treated; each unit containing a predetermined quantity of compound(s) calculated to produce the desired therapeutic effect in association with the required pharmaceutical carrier. The compound(s) may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

In one embodiment, the carrier may be an orally administrable carrier.

Another form of a pharmaceutical composition is a dosage form formulated as enterically coated granules, tablets or capsules suitable for oral administration.

Also included in the scope of this invention are delayed or extended release formulations.

In a preferred embodiment, the compound(s) of the invention may be administered by injection. In the case of injectable solutions, the carrier may be a solvent or dispersion medium containing, for example, water (eg, water-for-injection), saline, 5% glucose solution, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants (eg, polysorbate 80). Prevention of the action of microorganisms can be achieved by including various anti-bacterial and/or anti-fungal agents. Suitable agents are well known to those skilled in the art and include, for example, parabens, chlorobutanol, phenol, benzyl alcohol, ascorbic acid, thimerosal, and the like. In many cases, it may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminium monostearate and gelatin.

Sterile injectable solutions can be prepared by incorporating the analogue in the required amount in an appropriate solvent with one or a combination of ingredients enumerated above, as required, followed by filtered sterilisation. Generally, dispersions may be prepared by incorporating the analogue into a sterile vehicle which contains a basic dispersion medium and the required other ingredients from those enumerated above.

Tablets, troches, pills, capsules and the like can also contain the following: a binder such as gum gragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavouring agent such as peppermint, oil of wintergreen, or cherry flavouring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the analogue, sucrose as a sweetening agent, methyl and propylparabens as preservatives, a dye and flavouring such as cherry or orange flavour. Of course, any Material used in preparing any dosage unit form should be pharmaceutically pure and substantially non-toxic in the amounts employed. In addition, the analogue can be incorporated into sustained-release preparations and formulations.

Preferably, the pharmaceutical composition may further include a suitable buffer to minimise acid hydrolysis. Suitable buffer agent agents are well known to those skilled in the art and include, but are not limited to, phosphates, citrates, carbonates and mixtures thereof.

Single or multiple administrations of the pharmaceutical compositions according to the invention may be carried out. One skilled in the art would be able, by routine experimentation, to determine effective, non-toxic dosage levels of the compound and/or composition of the invention and an administration pattern which would be suitable for treating the diseases and/or infections to which the compounds and compositions are applicable.

Further, it will be apparent to one of ordinary skill in the art that the optimal course of treatment, such as the number of doses of the compound or composition of the invention given per day for a defined number of days, can be ascertained using convention course of treatment determination tests.

Generally, an effective dosage per 24 hours may be in the range of about 0.0001 mg to about 1000 mg per kg body weight; suitably, about 0.001 mg to about 750 mg per kg body weight; about 0.01 mg to about 500 mg per kg body weight; about 0.1 mg to about 500 mg per kg body weight; about 0.1 mg to about 250 mg per kg body weight; or about 1.0 mg to about 250 mg per kg body weight. More suitably, an effective dosage per 24 hours may be in the range of about 1.0 mg to about 200 mg per kg body weight; about 1.0 mg to about 100 mg per kg body weight; about 1.0 mg to about 50 mg per kg body weight; about 1.0 mg to about 25 mg per kg body weight; about 5.0 mg to about 50 mg per kg body weight; about 5.0 mg to about 20 mg per kg body weight; or about 5.0 mg to about 15 mg per kg body weight.

Alternatively, an effective dosage may be calculated according to the Body Surface Area (BSA) of the patient to be treated. The BSA of a patient may be readily calculated using methods known to those skilled in the art. A suitable dose generally may be up to about 500 mg/m$^2$. For example, generally, an effective dosage any be in the range of about 10 to about 500 mg/m$^2$, about 25 to about 350 mg/m$^2$, about 25 to about 300 mg/m$^2$, about 25 to about 250 mg/m$^2$, about 50 to about 250 m g/m$^2$, and about 75 to about 150 mg/m$^2$.

The invention will now be described with reference to the following non-limiting examples.

EXAMPLES

Example 1

Synthesis of Dp4Cych4mT, Dp4e4mT and Corresponding Hydrochloric Salts

Methodology:

The chelators di-2-pyridylketone 4-ethyl-4-methyl-3-thiosemicarbazone (Dp4e4mT) and di-2-pyridylketone 4-cyclohexyl-4-methyl-3-thiosemicarbazone (Dp4cycH4mT) were synthesized using a combination of established methods (Scovill, J P (1990). *Phosphorous, Sulphur and Silicon* 60: 15-19; Richardson, D. R. et al (2006).*J Med Chem*. 49: 6510-6521). Briefly, carbon disulphide (0.2 mol) was added dropwise to N-methylcyclohexylamine or N-ethylmethylamine (0.2 mol) in NaOH solution (250 mL, 0.8 M) and allowed to react until the organic layer almost disappeared. Next, sodium chloroacetate (0.2 mol) was added to the aqueous extract and allowed to react over-night at room temperature. The addition of concentrated HCl (25 mL) gave the solid carboxymethyl thiocarbamate intermediate. Approximately 0.08 mol of carboxymethyl thiocarbamate intermediate was dissolved in 20 mL hydrazine hydrate plus 10 mL of water. This was followed by five cycles of gentle heating (until fuming) and cooling. The solution was then allowed to stand until fine white crystals of thiosemicarbazide intermediate formed. A solution of the thiosemicarbazide intermediate (10 mmol) in water (15 mL) was added to di-2-pyridyl ketone (10 mmol) dissolved in EtOH (15 mL). Next, 5 drops of glacial acetic acid were added and the mixture was refluxed for 2 h and cooled to 5° C. to give the yellow Dp4cycH4mT or Dp4e4mT precipitate, respectively. Finally, Dp4cycH4mT or Dp4e4mT was dissolved in minimum volume of cold hexane and equimolar HCl was added to give the corresponding HCl salt. The synthesis scheme is shown in FIG. 1B.

Results:

Dp4cycH4mT: Yield 64% (from CS$_2$). Anal. calcd. For C$_{19}$H$_{23}$N$_5$S: C, 64.56; H, 6.56; N, 19.81%. Found: C, 64.51; H, 6.47; N, 20.04%.

Dp4cycH4mT.HCl.5H$_2$O Yield 87% (from Dp4cycH4mT). Anal. calcd. For C$_{19}$H$_{23}$N$_5$S.HCl 5.5H$_2$O: C, 47.54; H, 7.14; N, 14.59%. Found: C, 47.06; H, 6.65; N, 14.95%. $^1$H-NMR (DMSO-d$_6$): δ 8.82 (d, 1H), 8.61 (d, 1H), 8.04-7.90 (m, 3H), 7.62-7.56 (t, 2H), 7.50-7.46 (t, 1H), 3.18 (s, 3H), 1.83-1.49 (m, 7H), 1.40-1.10 (m, 3H). MS m/z (%) 376.3 (M+H, 5), 376 (M+Na, 34).

Dp4e4mT: Yield 44% (from CS$_2$). Anal. calcd. For C$_{15}$H$_{16}$N$_4$S: C, 63.4; H, 5.7; N, 19.7%. Found: C, 62.8; H, 5.9; N, 19.5%.

Dp4e4mT.HCl.5.5H$_2$O Yield 91% (from Dp4e4mT). Anal. calcd. For C$_{15}$H$_{17}$N$_5$S.HCl 5.5H$_2$O: C, 41.42; H, 6.72; N, 16.10%. Found: C, 41.31; H, 6.45; N, 15.95%. $^1$H-NMR (DMSO-d$_6$): δ 8.84 (d, 1H), 8.66 (d, 1H), 8.13-8.09 (t, 1H), 8.04-7.97 (dt, 2H), 7.67-7.59 (dt, 3H), 3.32 (s, 3H), 1.20 (s, 3H). MS m/z (%) 322.0 (M+Na, 46), 620.87 (M; dimer, +Na, 100).

Example 2

Anti-Proliferative Activity of Dp4e4mT and Dp4cycH4mT

Methodology:

SK-N-MC human neuroepithelioma cells were obtained from the American Type Culture Collection (ATCC; Rockville, Md., USA) and cultured according to the methods described previously (Richardson, D R et al (1995). *Blood* 86: 4295-306). The cells were maintained in minimum essential media (MEM; Invitrogen, CA, USA) which contained 10% fetal calf serum (FCS; JRH Biosciences, Kansas, USA), 1% non-essential amino acids (Gibco, Victoria, Australia), 1% penicillin/streptomycin/glutamine (Gibco, VIC, Australia) and fungizone (0.28 ng/mL; Squibb Pharmaceuticals, Montreal, Canada).

The pancreatic cancer cell lines, including MIAPaCa-2, PANC 1, CAPAN-2 and CFPAC-1 were a generous gift from Prof. Andrew Biankin (Garvan Institute, NSW, Australia). The MIAPaCa-2, PANC 1 and CFPAC-1 cell lines were grown in DMEM medium (Invitrogen) and CAPAN-2 cells were grown in McCoy's medium (Invitrogen). All media was supplemented with 10% (v/v) fetal calf serum (Invitrogen), 1% (v/v) non-essential amino acids (Invitrogen), 1% (v/v) sodium pyruvate (Invitrogen), 2 mM L-glutamine (Invitrogen), 100 µg/mL of streptomycin (Invitrogen), 100 U/ml penicillin (Invitrogen), and 0.28 µg/mL of fungizone.

Results:

The ability of the compounds to inhibit cellular proliferation was assessed initially in SK-N-MC cells by the MTT assay. Both Dp4e4mT and Dp4cycH4mT exhibited anti-proliferative activity significantly greater than that of DFO ($p<0.05$) and the iron chelator 2-hydroxy-1-naphthylaldehyde isonicotinoyl hydrazone (311) ($p<0.05$) in SK-N-MC cells (FIG. 2; Table 1), with $IC_{50}$ values of 0.0041 and 0.013 µM respectively.

Table 1. Anti-proliferative activity of Dp4e4mT and Dp4cycH4mT against SK-N-MC neuroepithelioma. $IC_{50}$ (µM) values of Dp4e4mT and Dp4cycH4mT in the SK-N-MC neuroepithelioma cell line as determine by the MTT assay. Cells were seed and allowed to attach to wells for 24 h and then incubated for 72 h at 37° C. with control medium or the chelators. Results are mean±SD (3 experiments)

|  | $IC_{50}$ (µM) |
|---|---|
| DFO | 13.4 ± 3.7 |
| 311 | 0.72 ± 0.32 |
| Dp4mT | 0.34 ± 0.11 |
| Dp4m4eT | 0.0041 ± 0.0015 |
| Dp4cycH4mT | 0.013 ± 0.0016 |

Figure 2:
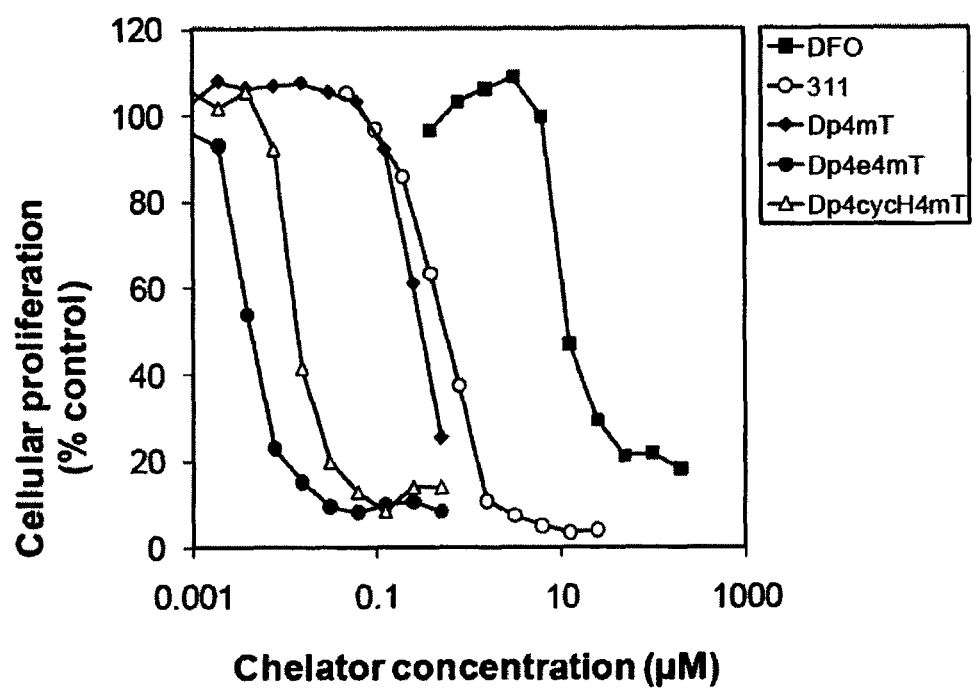

The chelators Dp4e4mT and Dp4cycH4mT are structurally-related to the compound di-2-pyridylketone 4-methyl-3-thiosemicarbazone (Dp4mT) through the replacement of a hydrogen atom at the terminal nitrogen (N4) by alkyl functional groups. The formation of Dp4e4mT involves the substitution of a hydrogen atom at N4 of Dp4mT with an ethyl group, whereas Dp4cycH4mT features a cyclohexyl substituent. These structural modifications were found to significantly ($p<0.001$) increase anti-proliferative activity of both analogues relative to Dp4mT, which has an $IC_{50}$ value of 0.34 µM (FIG. 2, Table 1).

To further examine the spectrum of anti-proliferative activity, Dp4cycH4mT was tested against pancreatic cancer in vitro, performing MTT proliferation assays with PANC 1, MIAPaCa-2, CFPAC-1 and CAPAN-2 pancreatic cancer cells. As a comparison, currently used treatments for pancreatic cancer including gemcitabine and 5-fluorouracil were also tested. The iron chelator, DFO, was included as a positive control.

In MIAPaCa-2, PANC 1 and CAPAN-2 cells, the highest anti-proliferative activity was observed with Dp4cycH4mT (FIGS. 3A, B and C) with $IC_{50}$ values being significantly ($p<0.01$) lower compared to gemcitabine and 5-fluorouracil (Table 2A). In fact, the $IC_{50}$ values for Dp4cycH4mT were at least 100-fold and 1000-fold lower in 2 out of the 4 cell types when compared to gemcitabine and 5-fluorouracil, respectively (Table 2A). The positive control, DFO, had relatively low anti-proliferative activity.

Table 2A. Anti-proliferative activity of Dp4cycH4mT against pancreatic cancer cell lines. Growth and antiproliferative activity $IC_{50}$ (µM) values of Dp4cycH4mT in a variety of pancreatic cell lines and in comparison to DFO and the clinically used drugs gemcitabine and 5-fluorouracil as determined by the MTT assay. Cells were seeded and allowed to attach to wells for 24 h and then incubated for 72 h at 37° C. with control medium or the chelators. Results are mean±SD (3 experiments).

| | $IC_{50}$ (µM) | | | |
|---|---|---|---|---|
| | DFO | Dp4cycH4mT | Gemcitabine | 5-fluorouracil |
| MIAPaCa-2 | 38.7 ± 6.2 | 0.009 ± 0.0003 | 0.02 ± 0.005 | 24.3 ± 6.3 |
| PANC 1 | 9.5 ± 1.4 | 0.05 ± 0.002 | 11.0 ± 0.8 | 62.3 ± 6.5 |
| CAPAN-2 | 7.0 ± 5.4 | 0.04 ± 0.008 | 40.8 ± 4.7 | 59.2 ± 24.2 |
| CFPAC-1 | 14.7 ± 3.1 | 0.4 ± 0.2 | 0.02 ± 0.02 | 41.2 ± 1.1 |

Figure 3:
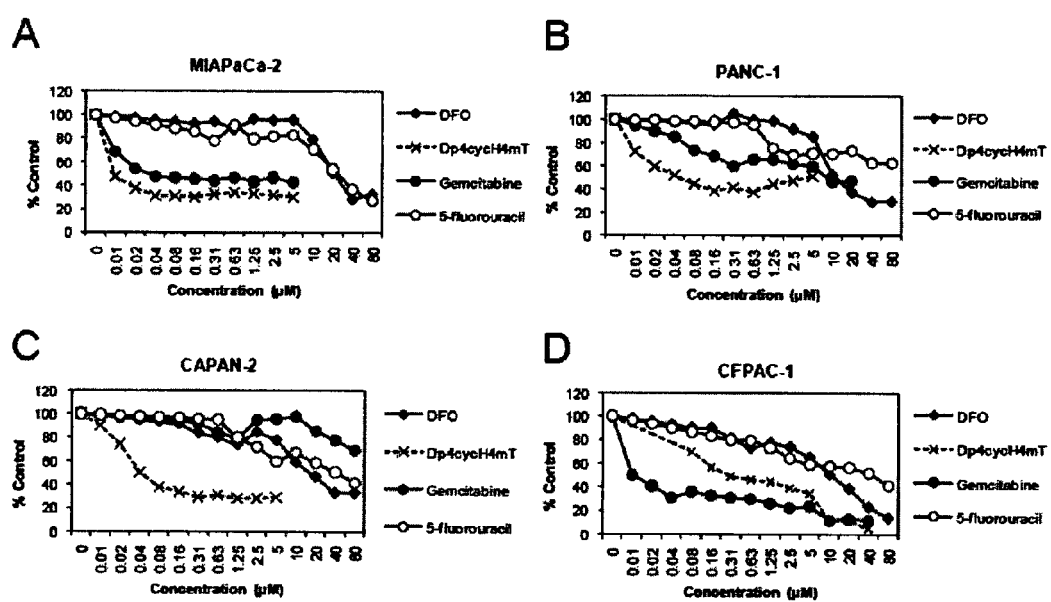
FIG. 3. Anti-proliferative activity of Dp4cycH4mT against pancreatic cancer cell lines including MIAPaCa-2 noted in Graph A, PANC-1 noted in Graph B, CAPAN-2 noted in Graph C, and CFPAC-1 noted in Graph D. MIAPaCa-2, PANC 1 and CAPAN-2 cells antiproliferative activity for Dp4cycH4mT (FIG. 3A, B and C). $IC_{50}$ value for gemcitabine compared to that of Dp4cycH4mT is shown in FIG. 3D.

In contrast to the other cell types, where the thiosemicarbazones had the highest anti-proliferative activity, CFPAC-1 cells were the most sensitive to gemcitabine. In fact, the $IC_{50}$ value for gemcitabine was significantly ($p<0.05$) lower than that of Dp4cycH4mT (FIG. 3D and Table 2A). Dp4cycH4mT had lower $IC_{90}$ values than gemcitabine in CFPAC-1 cells (FIG. 3D, Table 2B). Thus, these data suggest that the thiosemicarbazones have the potential to almost completely inhibit proliferation of this cell type in vitro when used at higher doses, while the anti-proliferative activity of gemcitabine is more limited (FIG. 3D) demonstrating the difference in response between the different cell types.

Table 2B. Anti-proliferative activity of Dp4cycH4mT against pancreatic cancer cell lines. $IC_{90}$ (µM) values of Dp4cycH4mT in a variety of pancreatic cell lines and in comparison to DFO and the clinically used drugs gemcitabine and 5-fluorouracil as determined by the MTT assay. Cells were seeded and allowed to attach to wells for 24 h and then incubated for 72 h at 37° C. with control medium or the chelators. Results are mean±SD (3 experiments).

| | $IC_{90}$ (µM) | | | |
|---|---|---|---|---|
| | DFO | Dp4cycH4mT | Gemcitabine | 5-fluorouracil |
| MIAPaCa-2 | >80 | >5 | >5 | >5 |
| PANC 1 | >80 | >5 | >5 | >20 |
| CAPAN-2 | >80 | >5 | >5 | >80 |
| CFPAC-1 | >80 | 5.4 ± 1.1 | 30.4 ± 2.2 | >40 |

Example 3

Cellular Fe Efflux and Inhibition of Fe Uptake from Transferrin by Dp4e4mT and Dp4cycH4mT Methodology:

Iron Efflux Assay

The effect of the iron chelators Dp4e4mT and Dp4cycH4mT on the release of $^{59}$Fe from pre-labeled SK-N-MCs neuroepithelioma cells were examined using established methods (eg, Baker, E et al (1992). *Hepatology* 15: 492-501). SK-N-MC cells were initially plated onto 35 mm culture dishes and incubated at 37° C. in a 5% $CO_2$/95% air humidified incubator until they were approximately 80% confluent. After this, the cells were pre-labeled through a 3 h incubation at 37° C. with appropriate media containing 0.06 mg/mL $^{59}$Fe-Tf (prepared as outlined in Baker, E et al (1992). *Hepatology* 15: 492-501). The culture dishes were then placed on ice, the supernatant containing excess $^{59}$Fe-Tf was aspirated and the cells washed 4 times with ice-cold PBS. The cells were then incubated for a further 3 h at 37° C. with media containing 25 µM chelators or media alone (control). After 3 h the culture dishes were again placed on ice, the media was collected in counting tubes and this provided a measurement of released $^{59}$Fe. Ice-cold PBS (1 mL) was added to plates containing cells and cells were scraped from the plastic surface using a Teflon spatula and also collected in counting tubes. These tubes represent the intracellular $^{59}$Fe content. Results are expressed as total $^{59}$Fe released as a percentage of total $^{59}$Fe present. Radioactivity was measured using a Wallac Wizard 3" Gamma Counter (PerkinElmer, MA, USA).

Iron Uptake Assay

The effect of the iron chelators Dp4e4mT and Dp4cycH4mT on the ability of SK-N-MCs to obtain $^{59}$Fe from media was examined using established methods (Richardson, D R, et al. (1995). *Blood* 86: 4295-306; Baker, E et al (1992). *Hepatology* 15: 492-501). Cells were cultured in the same way as for the iron efflux experiments. Once the cells were approximately 80% confluent they were incubated for 3 h at 37° C. with media containing 25 µM chelators or media alone (control). $^{59}$Fe-Tf (0.06 mg/mL) was added to the media. At the end of the incubation the culture dishes were placed on ice, the media aspirated, and the cells washed 4 times with ice cold PBS. Protease (1 mL; 1 mg/mL; Sigma-Aldrich, NSW, Australia) solution was added to each plate and allowed to incubate on ice for 30 min. This facilitated the removal of membrane bound $^{59}$Fe-Tf. Cells were then scraped from the plastic surface using a Teflon spatula and collected in Eppendorf tubes. These were centrifuged at 10000 rpm and 4° C. for 3 min. The supernatant was then transferred into counting tubes and the cell pellet resuspended in PBS before also being transferred into another set of counting tubes. Radioactivity was measured using a Wallac Wizard 3" Gamma Counter (PerkinElmer, MA, USA). Results are expressed as average $^{59}$Fe content of the cellular fraction as a percentage of the control value.

Example 3a

Cellular Fe Efflux Mediated by Dp4e4mT and Dp4cycH4mT

Figure 4:
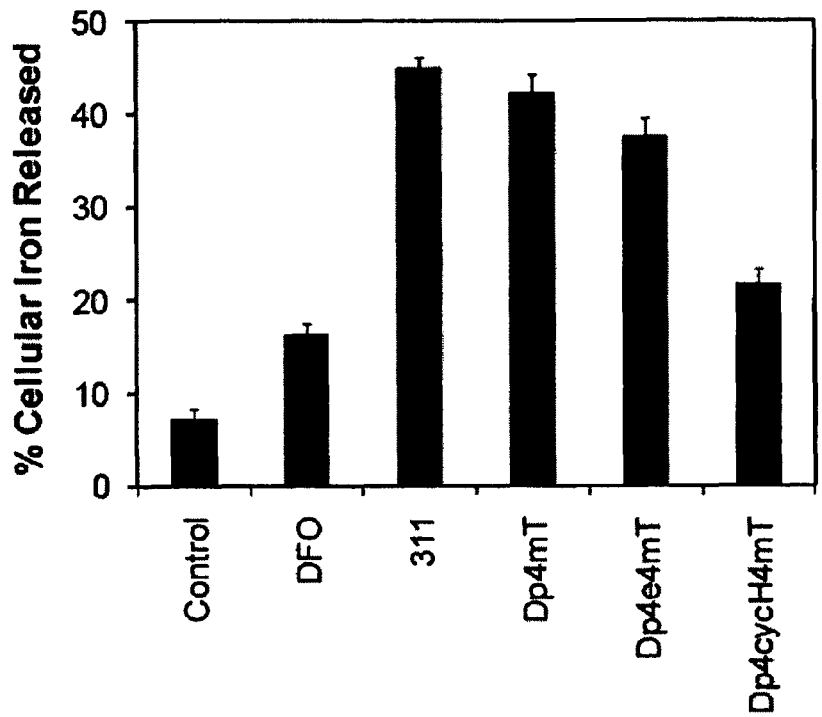
FIG. 4. Iron efflux (A) and iron uptake (B) studies in SK-N-MC neuroepithelioma cells. All dipyridyl thiosemicarbazone compounds exhibited significantly increased iron efflux activity compared to control cells (p<0.001) (FIG. 4A). Dp4e4mT, Dp4mT and DFO cellular $^{59}$Fe uptake are noted in FIG. 4B.
Figure 4:
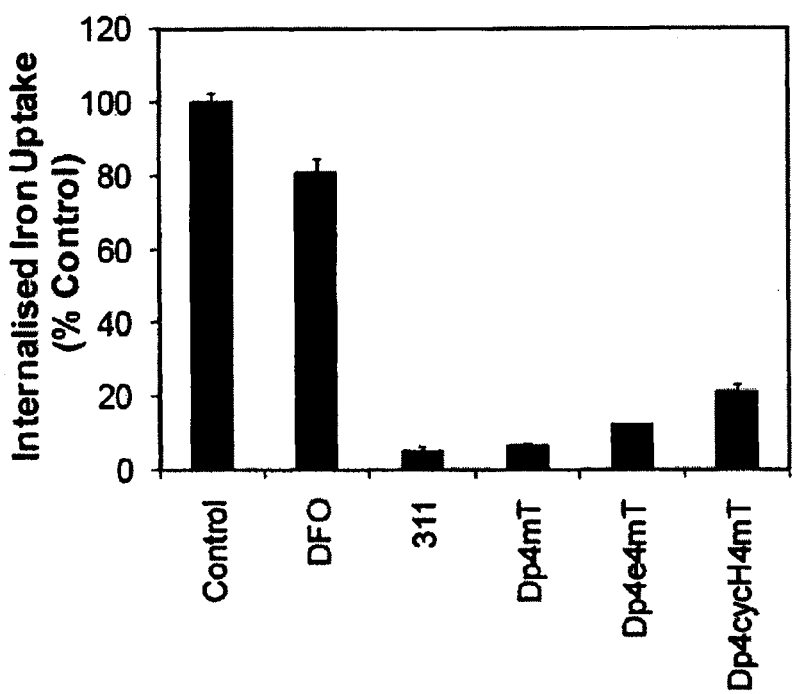

All dipyridyl thiosemicarbazone compounds exhibited significantly increased iron efflux activity compared to control cells ($p<0.001$) (FIG. 4A). Control cells released 7% of the total cellular $^{59}$Fe after a 3 h re-incubation with fresh media (FIG. 4A). The compound Dp4e4mT was able to mobilise 38% of cellular $^{59}$Fe (FIG. 4A), which was comparable to the compound Dp4mT, which mobilised 42% cellular Fe. The compound Dp4cycH4mT only mobilised 22% of cellular $^{59}$Fe, which was similar to the clinically used chelator DFO that mobilised 16% of cellular Fe, but less than the structurally related analogue Dp4mT (FIG. 4A). This suggests that Dp4cycH4mT may have other mechanisms of action besides Fe chelation considering its marked anti-proliferative activity relative to DFO and Dp4mT (Table 1). The iron efflux profile of the compound 311 was also examined as an internal standard and agreed with previous studies.

Example 3b

Inhibition of Cellular $^{59}$Fe Uptake from $^{59}$Fe Transferrin by Dp4e4mT and Dp4cycH4mT To further characterise Fe chelation efficacy, the ability of Dp4e4mT and Dp4cycH4mT to inhibit the uptake of $^{59}$Fe from $^{59}$Fe-Tf was compared to the structurally related compound, Dp4mT. Dp4e4mT limited cellular $^{59}$Fe uptake to 12% of the control, which was comparable to Dp4mT, which limited cellular $^{59}$Fe uptake to 6% of the control (FIG. 4B). Dp4cycH4mT was less effective than either Dp4e4mT or Dp4mT, limiting $^{59}$Fe uptake to 21% (FIG. 4B). However, all compounds showed considerably greater activity than DFO ($p<0.001$), which limited $^{59}$Fe uptake to only 84% of what was seen in untreated cells (FIG. 4B). Similarly to the iron efflux studies, the compound 311 was also examined as an internal standard and limited cellular $^{59}$Fe uptake to 5% which agreed with previous studies (eg, Richardson, D R et al. (1995). *Blood* 86: 4295-306).

Example 4

In-vivo Inhibition of Tumour Growth by Dp4e4mT and Dp4Cych4mT

Figure 5:
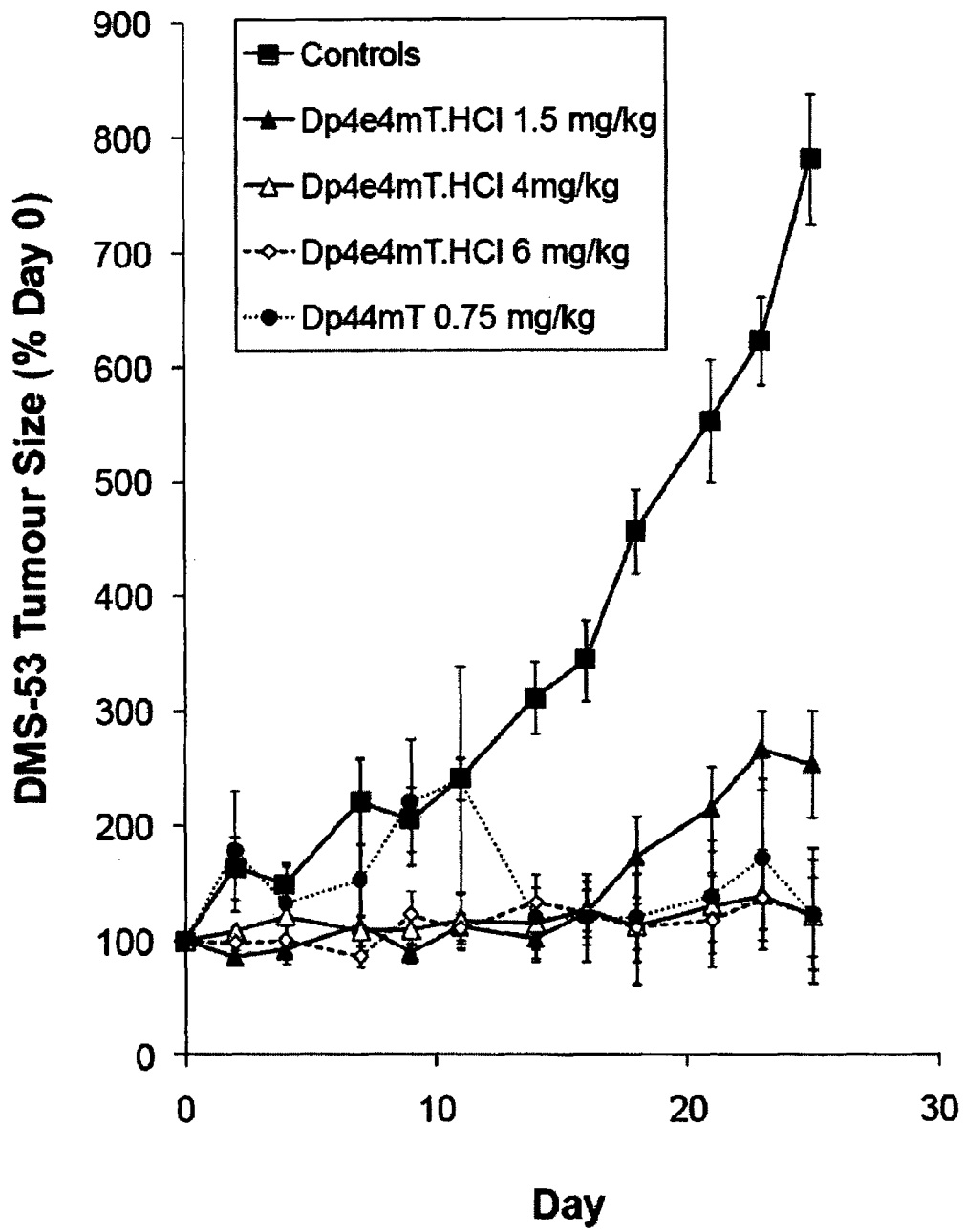
FIG. 5. Growth of DMS-53 lung carcinoma in nude mice. Dp4e4mT i.v administration study.

Methodology:

Female nude mice (BALBc nu/nu), 8-weeks old, were used for the in vivo studies and all studies were approved by the Animal Ethics Committee (University of Sydney). Tumor xenografts established by standard techniques (Whitnall, M, J. Howard, et al. (2006). *Proc Natl Acad Sci USA* 103: 14901-6.). In studies examining the growth of DMS-53 lung carcinoma, exponentially growing cells were harvested and a 1:1 mixture of cell-containing medium and Matrigel® (BD Biosciences, MA, USA) prepared using $1 \times 10^7$ cells/100 µL. The cell/matrigel mixture was injected s.c. into the right flank of methoxyflurane-anesthetised mice. In studies examining the growth of PANC 1 pancreatic cancer cells, each mouse was injected subcutaneously with $2 \times 10^6$ PANC 1 cells suspended in Matrigel (BD Biosciences, San Jose, Calif., USA). Tumor size was measured by Vernier calipers and tumour volume calculated as described previously (Balsari, A., M. Tortoreto, et al. (2004). *Eur J Cancer* 40: 1275-81.). Once the tumours reached an average of 90 mm$^3$, the treatment began (Day 0; FIG. 5).

Dp44mT and Dp4cycH4mT.HCl were dissolved in 30% propylene glycol in 0.9% saline and injected intravenously (via the tail vein) 5 days/week or given by oral gavage 5 days/week at the dosage specified in the respective study.

In the PANC 1 study, gemcitabine was dissolved in 15% propylene glycol in 0.9% saline and injected intra-peritoneally every 3$^{rd}$ day and each group (n=8) received either gemcitabine (5 mg/kg), Dp44mT (0.4 mg/kg), Dp4cycH4mT.HCl (5 mg/kg) or vehicle control. In the PANC 1 study, the vehicle control group was subdivided into two groups (n=4) with one receiving an intravenous injection of 30% propylene glycol in 0.9% saline 5 days/week, which acted as a control for the iron chelator treatment group. The other group received 15% propylene glycol in 0.9% saline intra-peritoneally every 3$^{rd}$ day and was the appropriate control for the gemcitabine treatment. Once control tumours reached 1,000 mm$^3$, the animals were euthanized due to ethical requirements.

Hematology, Biochemistry and Histology:

Upon completion of the in vivo experiment, blood was collected by cardiac puncture and hematologic indices assayed by standard methods (Dunn, L. L, et al (2006) *Carcinogenesis* 27: 2157-69). Tissues, including organs and tumours, were embedded in paraffin blocks and sectioned. Three different stains were utilized, namely hematoxylin and eosin (H & E), Pearl's or Gomori-Trichrome. In the PANC 1 tumour xenograft study, the histological analysis and quantification of pathological features was performed by an independent veterinary pathologist (Dr Terrence Rothwell, Rothwell Consulting, Avalon Beach, NSW, Australia).

Statistical Analysis:

Data were compared by using Student's t-test. Results were expressed as mean±SEM unless otherwise indicated. Data were considered statistically significant when $p<0.05$.

Example 4a

Effect of Dp4e4mT.HCl by i.v Administration on the in-vivo Inhibition of DMS-53 Human Lung Carcinoma A potent response to Dp4e4mT.HCl was observed in the DMS-53 xenograft model in nude mice (FIG. 5). After 25 days, average net tumour size in control vehicle-treated mice was 780% of the initial tumour volume, while in mice treated with 4 or 6 mg/kg Dp4e4mT, net tumour size was 120-122% of the initial volume. This was comparable to the degree of tumour inhibition exhibited by 0.75 mg/kg Dp44mT which inhibited the growth of the tumour to 122% of the initial tumour volume (FIG. 5).

Example 4a(i)

Biologic Assessment Following i.v. Dp4e4mT Treatment: Weight Loss and Hematological Analyses in Mice Bearing DMS-53 Human Lung Carcinoma In the DMS-53 lung carcinoma, study mice treated i.v. with 0.75 mg/kg Dp44mT lost 9% of initial weight (Table 3). In contrast, mice treated with Dp4e4mT.HCl at 4 or 6 mg/kg experienced weight loss of 0.6% and 7% of initial body weight, respectively, (Table 3) after 25 days of treatment. Control mice in this experiment lost 6% of initial body weight (Table 3).

TABLE 4

Growth of DMS-53 Lung carcinoma in nude mice Dp4e4mT i.v. administration study: Haematology.

| | WBC (10 × 9 cells/L) | RBC (10 × 12 cells/L) | HGB (g/L) | HCT | PLT (10 × 9 cells/L) |
|---|---|---|---|---|---|
| Controls | | | | | |
| Average | 2.77 | 10.03 | 144.67 | 0.44 | 874.67 |
| STD | 0.57 | 0.13 | 8.5 | 0.03 | 655.79 |
| Dp4e4mT•HCl (1.5 mg) | | | | | |
| Average | 3.34 | 8.76 | 150.60 | 0.4 | 766.4 |
| STD | 1.12 | 3.31 | 7.99 | 0.14 | 684.19 |
| Dp4e4mT•HCl (4 mg) | | | | | |
| Average | 2.94 | 10.74 | 153.75 | 0.47 | 1224.5 |
| STD | 0.56 | 0.33 | 4.92 | 0.01 | 713.7 |
| Dp4e4mT•HCl (6 mg) | | | | | |
| Average | 4.63 | 9.33 | 132.33 | 0.41 | 1238 |
| STD | 2.46 | 1.01 | 16.26 | 0.05 | 729.11 |
| Dp44mT (0.75 mg) | | | | | |
| Average | 5.38 | 9.87 | 135.50 | 0.43 | 1274.50 |
| STD | 1.46 | 0.83 | 10.61 | 0.01 | 43.13 |

WBC—white blood cell;
RBC—red blood cell;
HGB—haemoglobin;
HCT—hemacrit;
PLT—platelet

TABLE 3

Growth of DMS-53 Lung carcinoma in nude mice Dp4e4mT i.v administration study: Body and organ weights (g).

| | Experimental Groups (n = 6) | | | | |
|---|---|---|---|---|---|
| Organ | Control | Dp4e4mT-HCl (6 mg/kg) | Dp4e4mT-HCl (4 mg/kg) | Dp4e4mT-HCl (1.5 mg/kg) | Dp44mT (0.75 mg/kg) |
| Body weight loss (% initial weight) | 95.45 ± 3.41 | 93.38 ± 3.96 | 99.41 ± 1.75 | 95.14 ± 0.97 | 91.01 ± 5.3 |
| Liver | 1.05 ± 0.13 | 1.1 ± 0.08 | 1.03 ± 0.02 | 1.01 ± 0.02 | 1.04 ± 0.05 |
| Spleen | 0.13 ± 0.02 | 0.089 ± 0.01 | 0.08 ± 0.003 | 0.11 ± 0.01 | 0.13 ± 0.02 |
| Kidney | 0.26 ± 0.02 | 0.27 ± 0.01 | 0.26 ± 0.01 | 0.26 ± 0.01 | 0.23 ± 0.01 |
| Heart | 0.09 ± 0.01 | 0.11 ± 0.01 | 0.1 ± 0.01 | 0.1 ± 0.004 | 0.11 ± 0.01 |
| Brain | 0.31 ± 0.02 | 0.36 ± 0.03 | 0.36 ± 0.01 | 0.26 ± 0.13 | 0.32 ± 0.01 |
| Tumour | 0.97 ± 0.08 | 0.04 ± 0.03** | 0.11 ± 0.09*** | 0.48 ± 0.6* | 0.1 ± 0.02** |

Results are mean ± SEM

*$p < 0.05$; $p < 0.01$; *$p < 0.001$ compared to vehicle control as determined by Student's T test In terms of haematology, after 2 weeks of treatment with Dp44mT at 0.75 mg/kg or Dp4e4mT.HCl at 1.5, 4 or 6 mg/kg, there was no significant change in red blood cell count, haemoglobin or white blood cell count (Table 4). This indicates that at the doses and administration schedule used Dp4e4mT.HCl was well tolerated.

Example 4a(ii)

Effects of Dp4e4mT on Tissue Histology Following i.v. Dp4e4mT Treatment in Mice Bearing DMS-53 Human Luna Carcinoma Histological assessment was performed on tissues from the i.v. DMS-53 human lung carcinoma experiment. Results are discussed comparing tissues from DMS-53 xenografted mice treated with vehicle, Dp44mT (2 weeks at 0.75 mg/kg) or Dp4e4mT.HCl (2 weeks at 4 mg/kg and 6 mg/kg). In hematoxylin and eosin (H & E) stained sections, no significant differences were found in the histology of the liver, spleen, kidney, brain or tumour from control and chelator treated mice.

Figure 6:
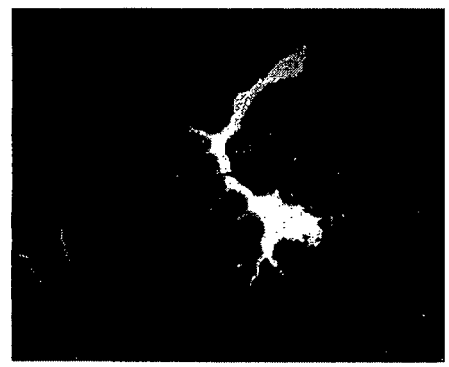
FIG. 6. Growth of DMS-53 lung carcinoma in nude mice. Dp4e4mT i.v administration study: assessment of cardiac fibrosis.
Figure 6:
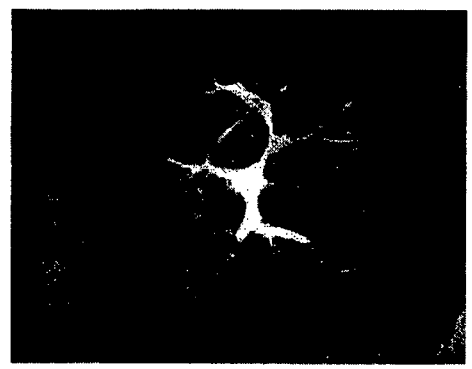
Figure 6:
Figure 6:
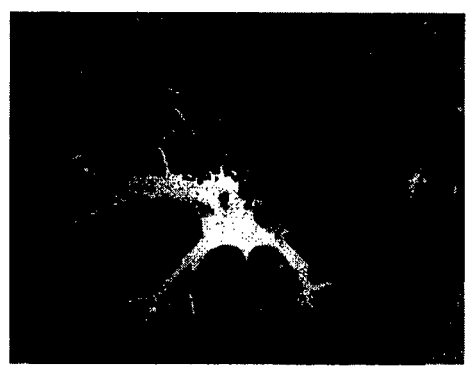
Figure 6:

However, myocardial lesions were observed in mice treated with Dp44mT (0.75 mg/kg; FIG. 6). Such lesions consisted of poorly differentiated foci of necrosis, being replaced with immature fibrous tissue which was evident using Gomori-Trichrome stain (arrow; FIG. 6) and was consistent with those described previously for Dp44mT (Whitnall, M., J. Howard, et al. (2006). *Proc Natl Acad Sci USA* 103: 14901-6). However, Dp4e4mT.HCl did not induce myocardial lesions at 4 mg/kg or 6 mg/kg after 2 weeks of i.v. administration (FIG. 6).

Example 4b

Figure 7:
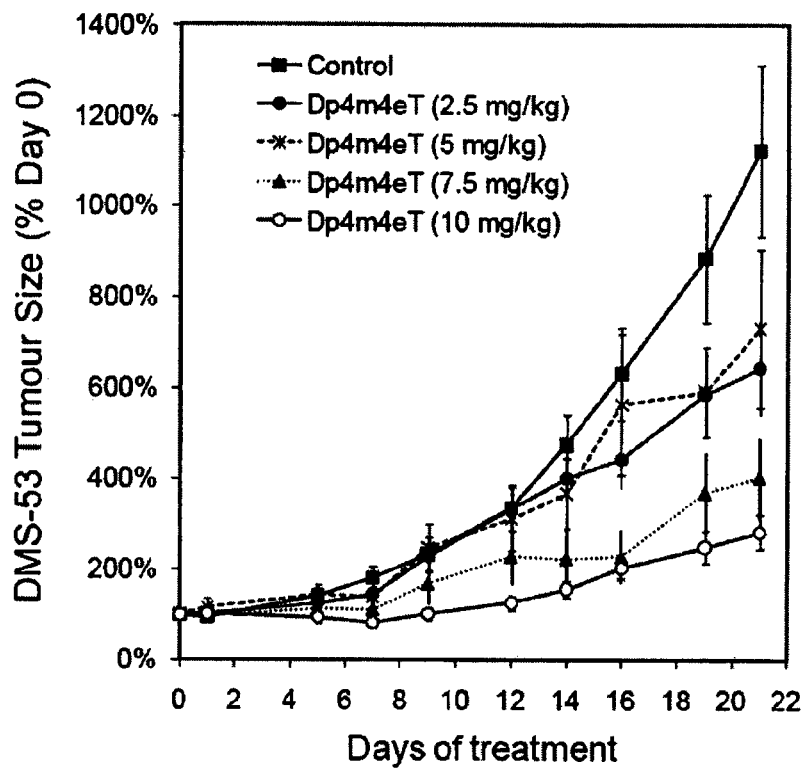
FIG. 7. Growth of DMS-53 lung carcinoma in nude mice. Dp4e4mT oral administration study: A. Tumour size v days of treatment. B. Tumour weight.
Figure 7:
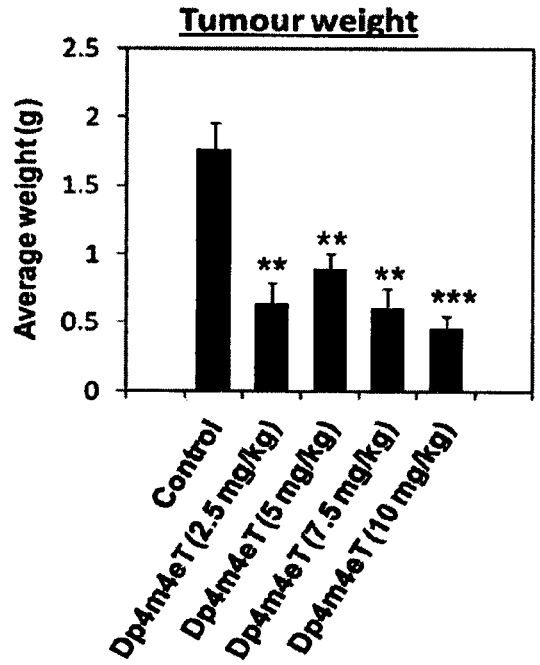

Effect of Dp4e4mT.HCl by Oral Administration on the in-vivo Inhibition of DMS-53 Human Lung Carcinoma Similarly to what was found when Dp4e4mT.HCl was given by i.v. administration (FIG. 5), a potent response to Dp4e4mT.HCl by oral gavage was observed in nude mice bearing the DMS-53 xenograft (FIG. 7A). After 21 days, average net tumour size in control vehicle-treated mice was 1124% of the initial tumour volume, while in mice treated with 7.5 or 10 mg/kg Dp4e4mT, the net tumour size was 404% and 284% of initial tumour volume, respectively (FIG. 7A). Lower doses of Dp4e4mT.HCl (2.5 and 5 mg/kg) also limited tumour growth to 645% and 733% of initial volumes, respectively (FIG. 7A).

Considering tumour weight, at end of the 21 day treatment period, untreated control mice had tumours that weighed, on average, 1.8 g (FIG. 7B). Mice treated with Dp4e4mT.HCl at 10 mg/kg by oral gavage showed a potent and significant ($p<0.0002$) decrease in average tumour weight to 0.46 g (FIG. 7B). Lower doses of Dp4e4mT.HCl by oral gavage also significantly inhibited tumour weight (FIG. 7B). For example, the lowest dose administered, 2.5 mg/kg, resulted in a significant ($p<0.002$) reduction in average tumour weight to 0.63 g (FIG. 7B).

Example 4b(i)

Biologic Assessment Following Oral Dp4e4mT Treatment: Weight Loss and Hematological Analyses in Mice Bearing DMS-53 Human Lung Carcinoma In the DMS-53 lung carcinoma study mice treated orally with Dp4e4mT.HCl, no treatment group showed any significant weight loss compared to the control group (Table 5). For example, control mice maintained 96% of their initial weight, whereas mice treated with the highest dose of Dp4e4mT.HCl (10 mg/kg) retained 94% of their initial weight; indicating that treatment at this dose was well tolerated (Table 5).

TABLE 5

Growth of DMS-53 Luna carcinoma in nude mice Dp4e4mT oral administration study: Body and organ weights (g).

| Organ | Control (n = 11) | Dp4e4mT (2.5 mg/kg) (n = 8) | Dp4e4mT (5 mg/kg) (n = 10) | Dp4e4mT (7.5 mg/kg) (n = 9) | Dp44mT (10 mg/kg) (n = 9) |
|---|---|---|---|---|---|
| Body weight (% initial) | 96.3 ± 1.7 | 94.1 ± 1.3 | 91.6 ± 2.4 | 91.6 ± 2.2 | 93.6 ± 1.8 |
| Liver | 0.84 ± 0.04 | 0.87 ± 0.02 | 0.77 ± 0.02 | 0.83 ± 0.03 | 0.88 ± 0.02 |
| Spleen | 0.082 ± 0.003 | 0.075 ± 0.004 | 0.075 ± 0.004 | 0.061 ± 0.009 | 0.081 ± 0.005 |
| Kidney | 0.205 ± 0.003 | 0.194 ± 0.005 | 0.187 ± 0.006 | 0.193 ± 0.008 | 0.208 ± 0.004 |
| Heart | 0.083 ± 0.002 | 0.078 ± 0.002 | 0.078 ± 0.002 | 0.092 ± 0.005 | 0.102 ± 0.005 |
| Brain | 0.367 ± 0.007 | 0.372 ± 0.006 | 0.367 ± 0.007 | 0.356 ± 0.007 | 0.363 ± 0.008 |
| Lung | 0.115 ± 0.003 | 0.121 ± 0.005 | 0.117 ± 0.003 | 0.119 ± 0.004 | 0.133 ± 0.008 |
| Tumour | 1.76 ± 0.24 | 0.63 ± 0.17** | 0.89 ± 0.14** | 0.60 ± 0.15** | 0.46 ± 0.1*** |

Values expressed as mean ± SEM.
*$p < 0.05$, $p < 0.01$, *$p < 0.001$ compared to vehicle control as determined by Students T-test In terms of haematology, after 21 days of treatment with Dp4e4mT.HCl at 2.5, 5, 7.5 or 10 mg/kg, there were significant changes in red blood cell count, haematocrit or white blood cell count (Table 6). Although at 5 mg/kg, Dp4e4mT.HCl significantly ($p<0.05$) reduced white blood cells and at 10 mg/kg significantly reduced haemoglobin ($p<0.05$) compared to untreated animals, however the clinical significance of these changes is not clear. Overall, haematology indicated the doses and administration schedule used Dp4e4mT.HCl was well tolerated.

Serum biochemical analysis showed that Dp4e4mT.HCl treatment at 5 mg/kg significantly ($p<0.05$) decreased 'total iron binding capacity' (TIBC) relative to the control (53.1±1.2 to 60.7±2 μmol/L, respectively; Table 6). However, higher dosage treatment groups did not show suppression of TIBC (Table 6). Additionally, 'unsaturated iron binding capacity' (UIBC) was significantly ($p<0.01$) increased in the 5 and 7.5 mg/kg Dp4e4mT.HCl treatment group relative to untreated controls but the 10 mg/kg treatment group did not show any significant change (Table 6). Alkaline phosphatase was also significantly elevated ($p<0.01$) in 10 mg/kg Dp4e4mT/HCl treated mice compared to untreated controls (89.5±4.5 to 68.7±12.8, respectively; Table 6) and was also significantly elevated in the 2.5 and 7.5 mg/kg groups (Table 6).

TABLE 6

Haematology and biochemistry

| | | Treatment Groups (Oral Gavage for 21 days, 3 days/week) | | | | |
|---|---|---|---|---|---|---|
| Indices | Units | Vehicle Control (n = 11) | Dp4e4mT 2.5 mg/kg (n = 8) | Dp4e4mT 5 mg/kg (n = 10) | Dp4e4mT 7.5 mg/kg (n = 9) | Dp4e4mT 10 mg/kg (n = 9) |
| Hematological indices | | | | | | |
| Red Blood Cell (RBC) | $10^{12}$/L | 10.92 ± 0.10 | 10.55 ± 0.12 | 10.26 ± 0.17 | 10.85 ± 0.14 | 10.18 ± 0.30 |
| White Blood Cell (WBC) | $10^{9}$/L | 2.62 ± 0.20 | 2.68 ± 0.53 | 1.80 ± 0.15* | 3.08 ± 0.43 | 3.27 ± 0.36 |
| Haemoglobin (HGB) | g/L | 156 ± 1 | 148 ± 2 | 143 ± 2 | 151 ± 2 | 142 ± 5* |
| Haematocrit (HCT) | % | 0.46 ± 0.004 | 0.44 ± 0.01 | 0.43 ± 0.01 | 0.45 ± 0.01 | 0.44 ± 0.01 |
| Platelets | $10^{9}$/L | 936 ± 79 | 1047 ± 73 | 973 ± 49 | 834 ± 114 | 917 ± 142 |
| Serum Biochemical indecs | | | | | | |
| Serum Iron | umol/L | 26.8 ± 2.1 | 25.5 ± 2.0 | 31.0 ± 1.9 | 32.8 ± 2.3 | 21.2 ± 2.0 |
| Total Iron-Binding Capacity (TIBC) | umol/L | 60.7 ± 2.0 | 56.7 ± 2.1 | 53.1 ± 1.2** | 56.8 ± 0.9 | 60.2 ± 2.3 |
| Unsaturated Iron-Binding Capacity (UIBC) | umol/L | 55.1 ± 2.5 | 57.9 ± 3.5 | 66.9 ± 2.3** | 64.9 ± 2.0** | 50.1 ± 2.7 |
| Alkaline Phosphatase (ALP) | U/L | 67.7 ± 5.7 | 85.7 ± 5.0* | 61.7 ± 2.0 | 87.2 ± 4.1* | 89.5 ± 4.5** |
| Alanine Aminotransferase (ALT) | U/L | 68.7 ± 12.8 | 73.1 ± 14.4 | 44.9 ± 2.8 | 57.2 ± 12.9 | 63.4 ± 9.9 |
| Albumin | g/L | 32.7 ± 0.6 | 31.3 ± 0.9 | 30.4 ± 0.5* | 31.3 ± 1.1 | 29.3 ± 1.6 |
| Cholesterol | mmol/L | 2.79 ± 0.19 | 2.44 ± 0.23 | 2.63 ± 0.12 | 2.78 ± 0.24 | 2.46 ± 0.16 |
| Triglyceride | mmol/L | 0.85 ± 0.12 | 1.00 ± 0.25 | 0.57 ± 0.05 | 0.67 ± 0.03 | 0.94 ± 0.98 |

Values expressed as mean ± SEM. *p < 0.05; p < 0.01; *p < 0.001 compared to their respectile vehicle control, as determined using Student's t-test.

Example 4b(ii)

Figure 8:
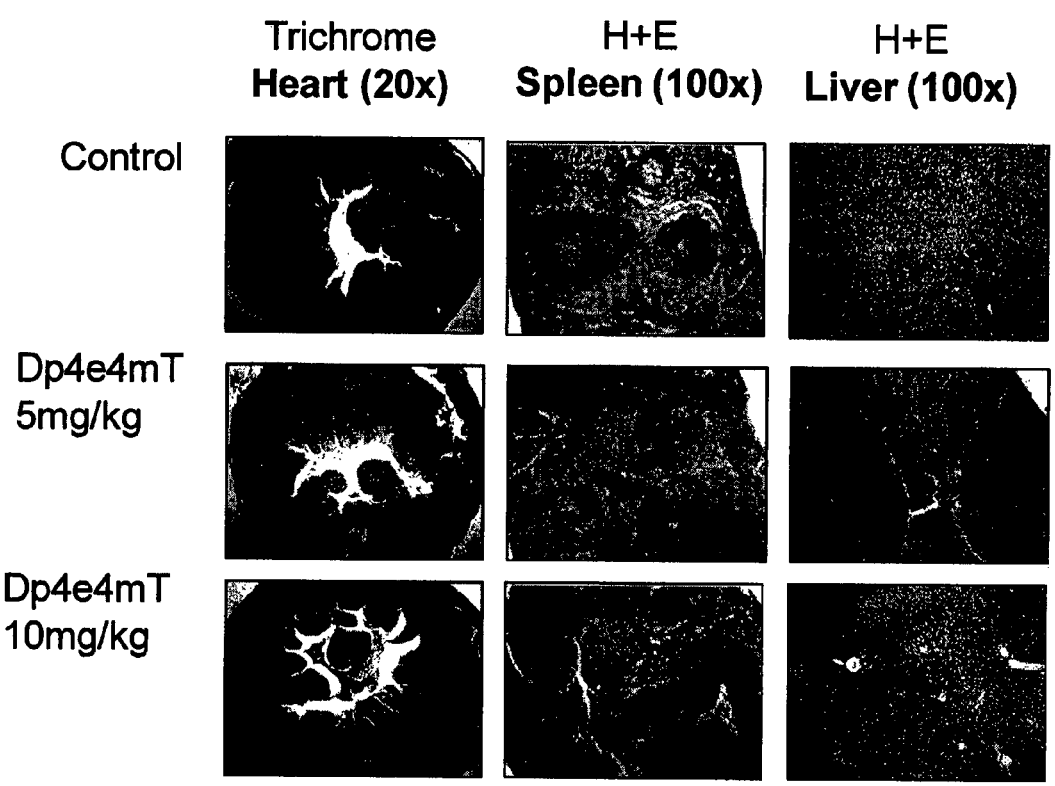
FIG. 8. DMS-53 lung carcinoma in nude mice. Dp4e4mT oral administration study: Histological analysis of heart, spleen, liver.

Effects of Dp4e4mT on Tissue Histology Following Oral Dp4e4 Mt Treatment in Mice Bearing DMS-53 Human Luna Carcinoma Histological assessment was performed on tissues from the oral DMS-53 human lung carcinoma experiment. Results are discussed comparing tissues from DMS-53 xenografted mice treated with vehicle, Dp44mT (2 weeks at 0.75 mg/kg) or Dp4e4mT.HCl (3 weeks at 2.5, 5, 7.5 and 10 mg/kg). In hematoxylin and eosin (H & E) stained sections, no significant differences were found in the histology of the liver, spleen, kidney, brain or tumour from control and thiosemicarbazone treated mice (FIG. 8).

However, myocardial lesions were observed in mice treated with Dp44mT (0.75 mg/kg; FIG. 8). Such lesions consisted of poorly differentiated foci of necrosis, being replaced with immature fibrous tissue which was obvious using Gomori-Trichrome stain (arrow; FIG. 8). However, Dp4e4mT.HCl did not induce myocardial lesions after 3 weeks at 2.5, 5, 7.5 and 10 mg/kg of oral administration (FIG. 8).

Example 4c

Effect of Dp4cycH4mT.HCl by i.v Administration on the in-vivo Inhibition of PANC 1 Human Pancreatic Carcinoma The in vitro analysis demonstrated that the thiosemicarbazones Dp44mT and Dp4cycH4mT.HCl are considerably more effective at inhibiting proliferation of a range of pancreatic cancer cell lines when compared to gemcitabine (FIG. 3A-C, Tables 2A and B). To further characterize the efficacy of the thiosemicarbazones against pancreatic cancer in vivo studies were performed.

Figure 9:
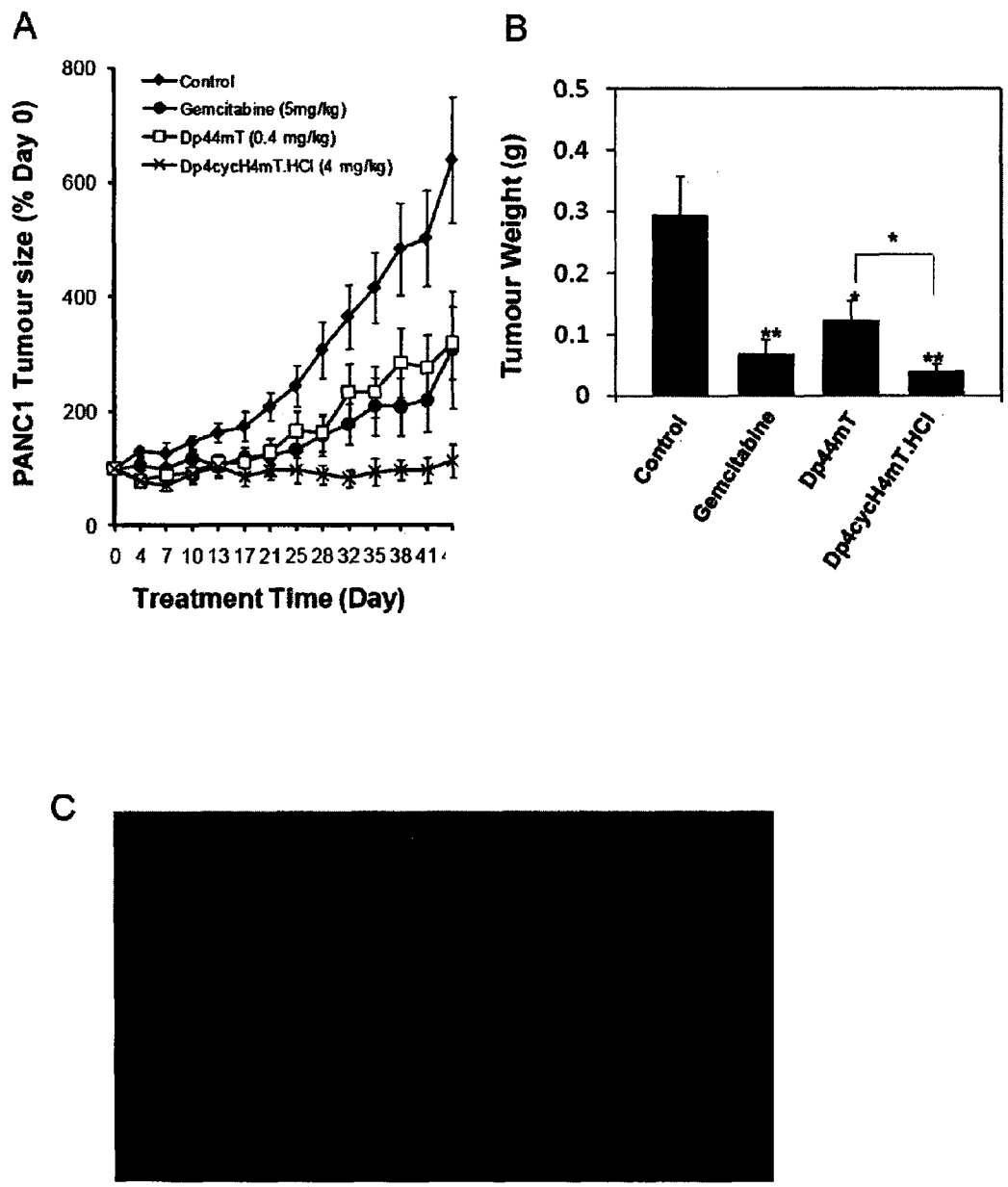
FIG. 9. Growth of PANC 1 pancreatic carcinoma in nude mice. Dp4cycH4mT i.v administration study: A. Tumour size v days of treatment. B. Tumour weight. C. Photographs of representative tumours.

Using PANC 1 xenografts, after 6 weeks of treatment the vehicle control mice had reached an average tumour size of approximately 640% of initial tumour volume while the groups treated with gemcitabine, Dp44mT and Dp4cycH4mT.HCl reached an average of 319%, 305% and 112% of the original tumour size, respectively (FIG. 9A). Gemcitabine (p<0.01), Dp44mT (p<0.05) and Dp4cycH4mT.HCl (p<0.001) all significantly reduced tumour volume relative to the control after 43 days of treatment.

Furthermore, the final tumour weights after 43 days of treatment reflected the tumour volumes with control tumours weighing an average of 292±65 mg while tumours treated with gemcitabine, Dp44mT and Dp4cycH4mT.HCl weighed an average of 67±25 mg, 122±33 mg and 40±12 mg, respectively (FIG. 9B). These results show that each treatment was able to significantly inhibit the growth and progression of the tumour xenograft in vivo.

Although the difference between Dp4cycH4mT.HCl and gemcitabine tumour volumes was not statistically significant (p>0.05), the data obtained indicates that after day 32, both gemcitabine and Dp44mT treatments were slightly less effective at inhibiting tumour growth when compared to Dp4cycH4mT.HCl (FIG. 9A). As the tumour size of the vehicle control group was the limiting factor in the duration of this experiment, it was not possible to continue further treatment after 43 days due to ethical limitations.

Example 4c(i)

Biologic Assessment Following i.v. Dp4cycH4mT.HCl Treatment: Weight Loss and Hematological Analyses in Mice Bearing PANC 1 Human Pancreatic Carcinoma To determine whether the different agents used in the in vivo studies above were associated with any toxicity, haematological indices as well as body and organ weights were analyzed following euthanasia.

TABLE 7A

Growth of PANC-1 pancreatic carcinoma in nude mice Dp4cycH4mT i.v administration study: Body and organ weights (g).

| | Experimental Group (n = 8) | | |
|---|---|---|---|
| Organ | Control | Dp4cycH4mT (5 mg/kg/day) | Gemcitabine (5 mg/kg/day) |
| Body weight loss (% initial weight) | 104.9 ± 4.6 | 88.0 ± 6.5*** | 104.5 ± 2.2 |
| Liver | 0.96 ± 0.11 | 0.80 ± 0.03 | 1.04 ± 0.03 |
| Spleen | 0.12 ± 0.01 | 0.08 ± 0.01** | 0.13 ± 0.01 |
| Kidney | 0.15 ± 0.02 | 0.17 ± 0.02 | 0.19 ± 0.03 |
| Heart | 0.10 ± 0.01 | 0.09 ± 0.01 | 0.10 ± 0.01 |
| Brain | 0.32 ± 0.02 | 0.30 ± 0.01 | 0.32 ± 0.01 |
| Tumour | 0.29 ± 0.07 | 0.04 ± 0.01*** | 0.07 ± 0.02** |

$p < 0.05$;
**$p < 0.01$;
***$p < 0.001$

Figure 10:
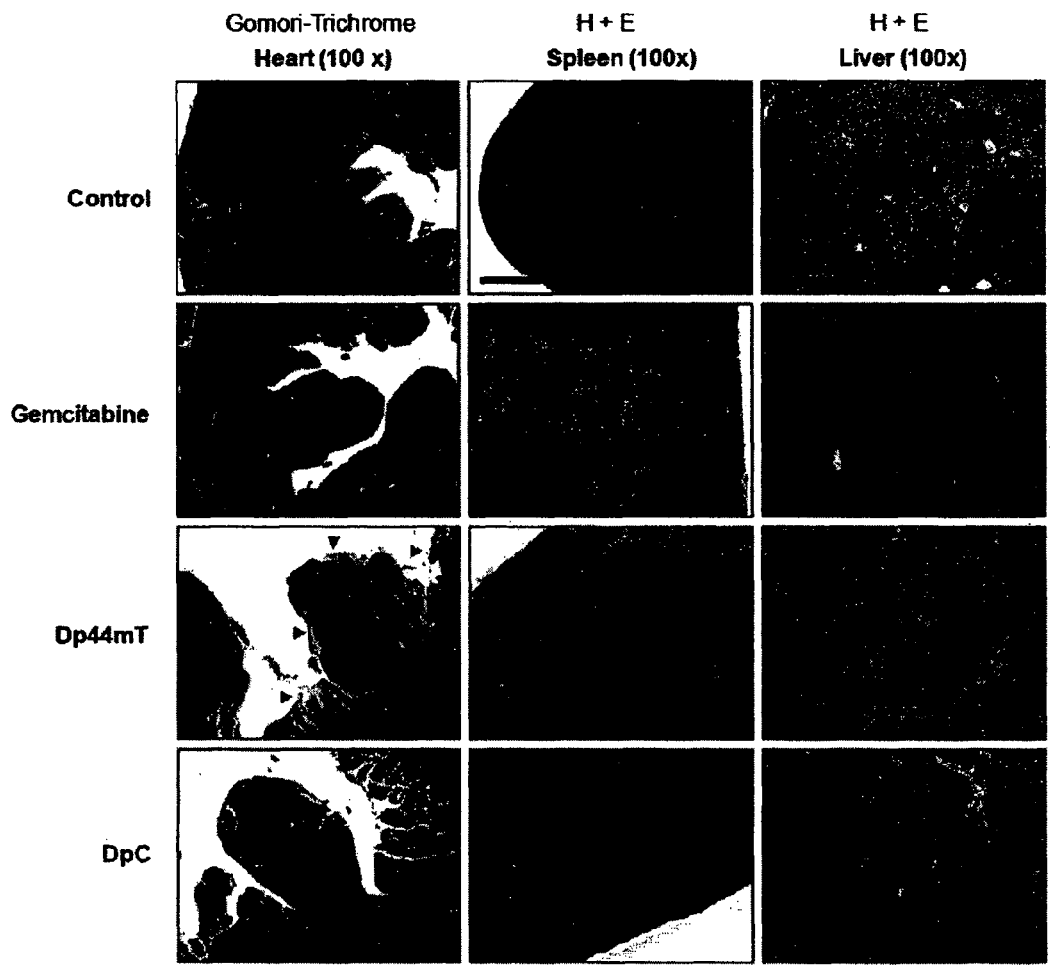
FIG. 10. Growth of PANC 1 pancreatic carcinoma in nude mice. Dp4cycH4mT i.v administration study: Histological analysis of heart, spleen, liver.

The body weight of the animals after 6 weeks of treatment remained close to 100% of the pre-treatment weight for each group with the exception of Dp4cycH4mT.HCl (Table 7A). These animals showed a significant ($p<0.001$) weight loss of 12% when compared to their pre-treatment weight (Table 7A). Although no significant differences in the organ weights was found (Table 7A) between the different treatment groups, it was observed that the Dp4cycH4mT.HCl group also had a significantly ($p<0.001$) smaller spleen when compared to the control group (Table 7A). A histological analysis of the spleen found that the splenic red pulp of mice in all groups contained a normal population of hematopoietic cells. Therefore, there was no evidence to suggest splenic toxicity (FIG. 10).

TABLE 7B

Growth of PANC 1 pancreatic carcinoma in nude mice Dp4cycH4mT i.v administration study: Haematology

| | Experimental Groups (n = 8) | | |
|---|---|---|---|
| | Control | Dp4cycH4mT (5 mg/kg/day) | Gemcitabine (5 mg/kg/3 days) |
| RBC × $10^{12}$/L | 10.17 ± 0.15 | 9.46 ± 0.31 | 9.65 ± 0.08 |
| Hb g/L | 146.44 ± 1.68 | 131.88 ± 4.31** | 147.88 ± 1.19 |
| HCT | 0.44 ± 0.01 | 0.41 ± 0.01 | 0.45 ± 0.01 |
| Platelets $10^9$/L | 1042 ± 147 | 1283 ± 160 | 1060 ± 205 |
| WBC × $10^9$/L | 4.53 ± 0.44 | 3.5 ± 0.34 | 5.51 ± 0.56 |
| Reticulocytes × $10^{12}$/L | 0.56 ± 0.06 | 0.77 ± 0.08* | 0.35 ± 0.12 |

$p < 0.05$,
**$p < 0.01$

Haematological indices, in particular signs of anaemia, was an important parameter to examine as the thiosemicarbazone compounds are iron chelators. No significant difference in the red blood cell (RBC), white blood cell (WBC) or platelet-counts was detected between control and the different treatment groups (Table 7B). However, the Dp44mT and Dp4cycH4mT.HCl groups had significantly ($p<0.01$) lower haemoglobin (Hb) and significantly ($p<0.05$) higher reticulocyte levels when compared to the control group (Table 7B). This may be an indicator of a slight anaemia in these animals.

Example 4c(ii)

Effects on Tissue Histology Following Oral Dp4cycH4mT.HCl Treatment in Mice Bearing PANC 1 Human Pancreatic Carcinoma To further investigate the potential toxic effects of the different treatments on the organs, a histological analysis of the spleen, kidney, liver, heart, lungs, brain and bone marrow was performed by staining with H&E (for general pathology), Pearls' (for presence of iron) and Gomori-Trichrome (for fibrosis). The histological analysis was performed by a veterinary pathologist and the results are presented in Table 8.

TABLE 8

Independent histopathological assessment

| Treatment Group | BONE HP | KIDNEY Fe | LIVER HP | LUNG HP | MYOCARDIUM HP | MYOCARDIUM Fibrosis | SPLEEN HPC |
|---|---|---|---|---|---|---|---|
| Control | N | + | N | N | N | − | N |
| | N | − | N | N | N | − | N |
| | N | − | N | N | N | − | N |
| | N | + | N | N | N | − | N |
| | N | ++ | N | N | N | − | N |
| | N | − | N | N | N | − | N |
| | N | − | N | +/− | N | − | N |
| | N | − | N | + | N | − | N |
| | N | +/− | N | N | N | − | N |
| | N | + | N | N | N | − | N |
| Gemcitabine | N | − | N | N | N | − | N |
| | N | − | N | N | N | − | N |
| | N | − | N | N | N | − | N |
| | N | − | N | N | N | − | N |
| | N | − | N | N | N | − | N |
| | N | − | N | N | N | − | N |
| | N | − | N | N | N | − | N |
| Dp44mT | N | ++ | N | N | ++ | ++ | N |
| | N | + | N | N | + | + | N |
| | N | ++ | N | +/− | + | + | N |
| | N | + | + | N | + | + | N |
| | N | + | ++ | + | + | + | N |
| | N | + | +/− | +/− | + | + | N |

TABLE 8-continued

| | Independent histopathological assessment | | | | | | |
|---|---|---|---|---|---|---|---|
| | BONE | KIDNEY | LIVER | LUNG | MYOCARDIUM | | SPLEEN |
| Treatment Group | HP | Fe | HP | HP | HP | Fibrosis | HPC |
| | N | + | ++ | N | + | + | N |
| | N | +/− | +/− | + | + | + | N |
| Dp4cycH4mT.HCl | N | + | N | N | N | − | N |
| | N | + | N | +/− | N | − | N |
| | N | + | +/− | N | N | − | N |
| | N | + | +/− | N | N | − | N |
| | N | + | +/− | N | N | − | N |
| | N | + | N | + | N | − | N |
| | N | + | N | N | N | − | N |
| | N | + | N | N | N | − | N |

HP—Histopathological changes; Fe—Score for presence of iron stained by Perl's stain; HPC—Score for the presence of haematopoietic cells in the splenic red pulp; N—No histopathological changes detected.
(−) No damage; (+/−) Very mild, localized damage; (+) Less than 10% damage; (++) Less than 20% damage.

Two of the Dp44mT-treated mice contained some evidence of haematopoietic cells in the liver. In addition, iron deposits were observed in the kidneys of 5 of the 10 control-treated mice and all the Dp44mT- and Dp4cycH4mT.HCl-treated animals (Table 8), which may be due to iron in the diet and the excretion of the iron complex formed by the thiosemicarbazone chelators in the urine, respectively. The gemcitabine-treated group had no evidence of iron deposits in the kidney (Table 8). The myocardium of each mouse in the Dp44mT group displayed myocardial lesions that were characterized by myocardial fibre degeneration and necrosis, with replacement by fibrous tissue (FIG. 10; Table 8). The pathological changes observed were most pronounced in the wall of the right ventricle and also in the myocardium beneath the endocardium of the left ventricle (FIG. 10). This is in agreement with an earlier study that also detected cardio-fibrosis in Dp44mT-treated nude mice. There was no significant evidence of fibrotic lesions in the heart of the Dp4cycH4mT.HCl-treated group, demonstrating that this compound was more potent and far less toxic than Dp44mT in vivo at higher doses.

Significantly, there was no evidence of pathology in any of the other organs examined (Table 8), suggesting that neither Dp4cycH4mT.HCl nor gemcitabine induced marked tissue damage when compared to the untreated controls.

Example 4d

Effect of Dp4cycH4mT on the Expression of the Metastasis Suppressor Protein NDRG-1. Transferrin Receptor and Cell-Cycle Control Molecules Methodology:
Western Blot Analysis Protein isolation was performed as described previously (Dunn, L. L., et al (2006) *Carcinogenesis* 27: 2157-69.

Western analysis was performed via established protocols (Gao, J. and D. R. Richardson (2001). *Blood* 98: 842-50). The primary antibodies used were against NDRG1 (Abcam; UK), p21, cyclin D1, transferrin receptor 1 (TfR1; Santa Cruz, CA, USA) and β-actin (Sigma-Aldrich), with secondary HRP-conjugated goat and mouse antibodies (Sigma-Aldrich).
Results:

Dp4cycH4mT was examined to determine whether it could up-regulate NDRG-1 expression. To further evaluate the effect of the chelator Dp4cycH4mT on other key molecules involved in cell cycle progression, the expression of the cyclin-dependent kinase inhibitor, p21, as well as cyclin D1 in MIAPaCa-2 cells was also examined. As a positive control for iron chelator treatment, transferrin receptor 1 (TfR1) was also examined, as this protein has previously been found to be up-regulated by thiosemicarbazone compounds.

Figure 11:
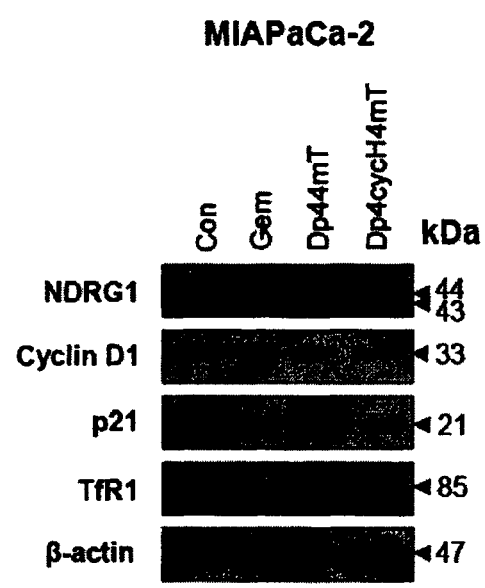
FIG. 11. Growth of PANC 1 pancreatic carcinoma in nude mice. Dp4cycH4mT i.v. administration study: effect of Dp4cycH4mT on NDRG-1, TfR and cell cycle molecules. Protein isolation by Western blot analysis (Graph A) and a bar plot of the results (Graph B) are provided.
Figure 11:
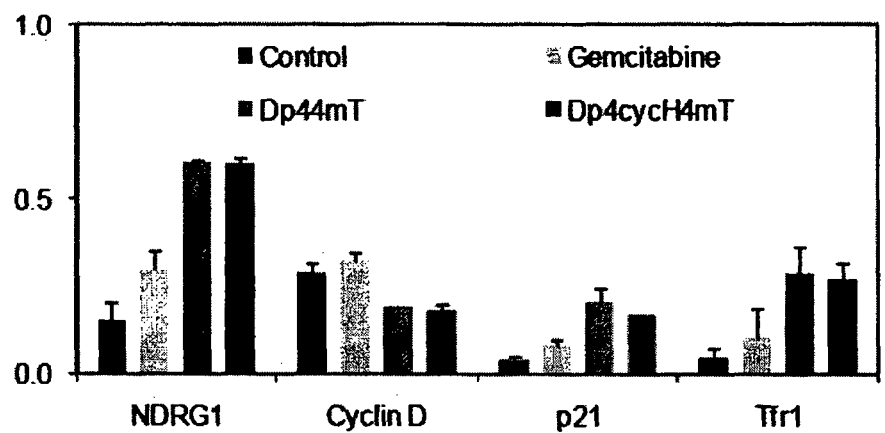

Both Dp44mT and Dp4cycH4mT significantly ($p<0.01$) up-regulated NDRG1 expression in MIAPaCa-2 cells, while gemcitabine had no marked effect (FIG. 11). In addition, Dp44mT and Dp4cycH4mT also significantly ($p<0.05$) reduced cyclin D1 levels while markedly ($p<0.05$) increasing p21 expression in these cells (FIG. 11). Moreover, TfR1 levels were also significantly ($p<0.05$) up-regulated in the MIAPaCa-2 cells following treatment with the thiosemicarbazone compounds, suggesting that these agents were effectively depleting the cells of iron (FIG. 11). On the other hand, gemcitabine treatment did not modulate cyclin D1, p21 or TfR1 levels in the MIAPaCa-2 cells (FIG. 11), indicating that its mechanism of action is different to that of the thiosemicarbazones.

Collectively, these results show that NDRG1 is markedly up-regulated by Dp4cycH4mT, suggesting that Dp4cycH4mT may be a beneficial treatment strategy against cancers by targeting NDRG1 expression in cancer cells.

Example 5

In vitro and in vivo Modulation of the Levels of Methemoulobin (metHb) and Metmyoglobin (metMb) by Iron Chelators Methodology
Chemicals Triapine® was synthesized and characterized according to published methods (Liu MC, Lin T C, et al (1992). *J Med Chem* 35: 3672-3677). Dp44mT, Bp4eT, DpC, di-2-pyridylketone-4-ethyl-4-methyl-3-thiosemicarbazone (Dp4e4mT), di-2-pyridylketone-4-phenyl-3-thiosemicarbazone (Dp4pT) and di-2-pyridylketone-2-methyl-3-thiosemicarbazone (Dp2mT) were also synthesized and characterized using published procedures. Richardson DR, Sharpe P C, et al (2006). *J Med Chem* 49:6510-6521; Kalinowski D S, Yu Y, et al, (2007). *J Med Chem* 50: 3716-3729). All other chemicals were purchased from Sigma-Aldrich (St. Louis, Mo., USA). For use in the assays described below, compounds were freshly prepared in DMSO and diluted (final [DMSO] <0.05%).
Red Blood Cell Isolation Whole blood samples were collected from healthy human donors or mice in suitable blood collection tubes containing EDTA and used immediately. Red blood cells (RBCs) were isolated by centrifugation (480 xg/5 min/4° C.) then washed in Hank's balanced salt solution (HBSS). RBCs were resuspended 1:1 in HBSS and whole RBC assays were carried out at 37° C.

Myoglobin Preparation

Mouse heart tissue was exhaustively perfused with ice-cold HBSS to remove blood and homogenized in ice-cold HBSS containing protease inhibitor cocktail (Roche, Basel, Switzerland). Heart homogenates were centrifuged (16,000× xg/45 min/4° C.) and the supernatant ([oxyMb]=50 µM) used immediately.

Measurement of metHb and metMb by UV-Vis Spectrophotometry

The levels of metHb and metMb in RBC lysates were determined using a Shimadzu UV-Vis spectrophotometer (UV-1800; Shimadzu Corporation, Kyoto, Japan) at 577 nm and 630 nm for metHb and metMb in accordance with published methods (Winterbourn CC and Carrell R W (1977). *Biochem J* 165: 141-148).

MetHb- and metMb-Formation in Mice

C57BL6 mice (7-8 weeks-old) were used under a protocol approved by the university of Sydney Animal Ethics Committee. Dp44mT, Triapine® or Dp4cycH4mT (all at 6 mg/kg) were dissolved in 30% propylene glycol/saline and administered iv via the tail vein. Subsequently, 30 min after administration, mice were anesthetized with isoflurane and blood samples obtained by cardiac puncture. Blood samples were lysed with 2.5 volumes of ultrapure water for metHb estimation. Mice were sacrificed with isoflurane, the heart exhaustively perfused with HBSS and Mb isolated.

Statistics

Data were compared using the Student's t-test. Results were considered significant when p<0.05. Results are mean±SD.

Example 5a

Ability of Iron Chelators to Induce MetHb-formation in Human RBCs

Figure 12:
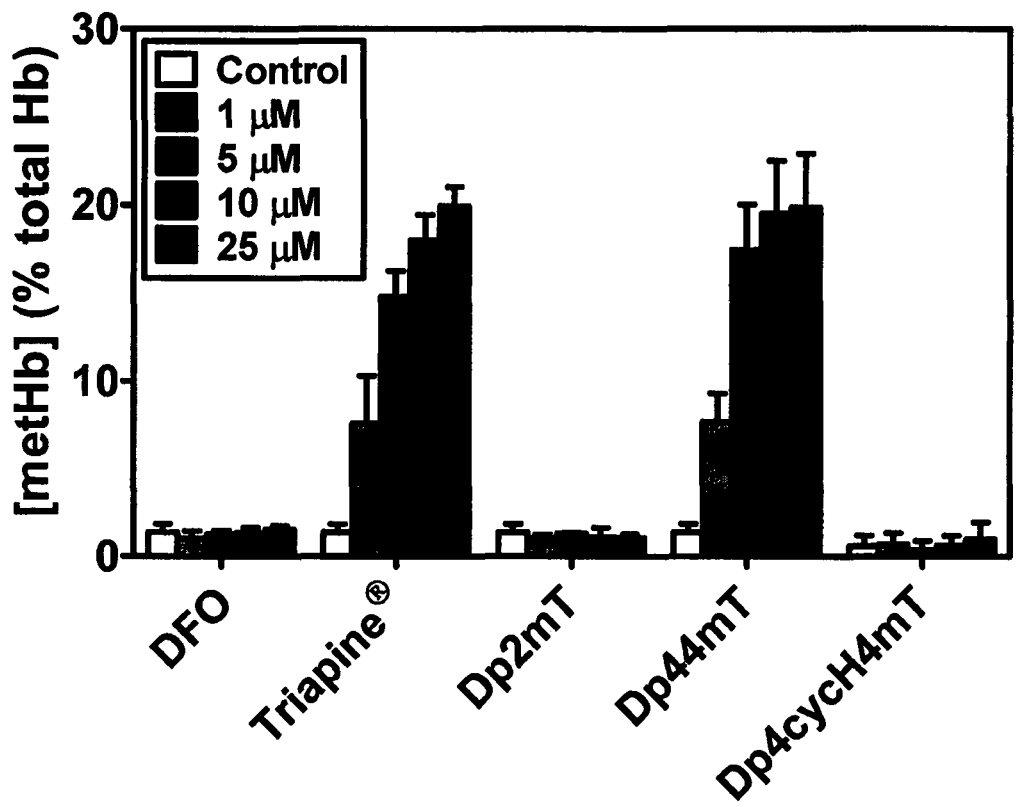
FIG. 12. Effect of DFO and thiosemicarbazone chelators on metHb-formation in vitro. Whole RBCs were incubated with 1-25 μM chelator at 37° C. for 3 h. Cells were lysed with ultra-pure $H_2O$ and metHb levels were measured spectrophotometrically. Results are the mean±SD from 3 experiments.

The effect of chelator concentration (1-25 µM) on metHb-generation with intact RBCs was assessed (FIG. 12). A significant (p<0.001) dose-dependent increase in metHb relative to the control was detected at all ligand concentrations in intact RBCs treated with Triapine® or Dp44mT after 3 h/37° C. (FIG. 12) which were the only chelators to demonstrate an ability to induce metHb formation. At 25 µM, these chelators increased metHb formation to 19.95±1.0 and 19.9±3.0% of total Hb, respectively (FIG. 12). The negative control chelator Dp2mT, by design, features a methyl group that hinders complex formation. Accordingly, this chelator cannot participate in the redox-interaction with iron that gives rise to metHb formation (FIG. 12). Additionally, the non-redox active chelator DFO, currently used as a treatment for iron overload disorders, also did not increase metHb formation.

Significantly, Dp4cycH4mT did not potentiate metHb formation in vitro (FIG. 12). This may constitute a clear advantage of DpcycH4mT therapy relative to Triapine®.

Example 5b

Ability of the Iron Chelators Triapine. Dp44mT and Dp4cycH4mT to Induce metHb Formation in vivo To confirm the in vitro results of Example 5a showing that Dp4cycH4mT did not potentiate metHb formation, metHb formation in a mouse model as described above was examined.

Figure 13:
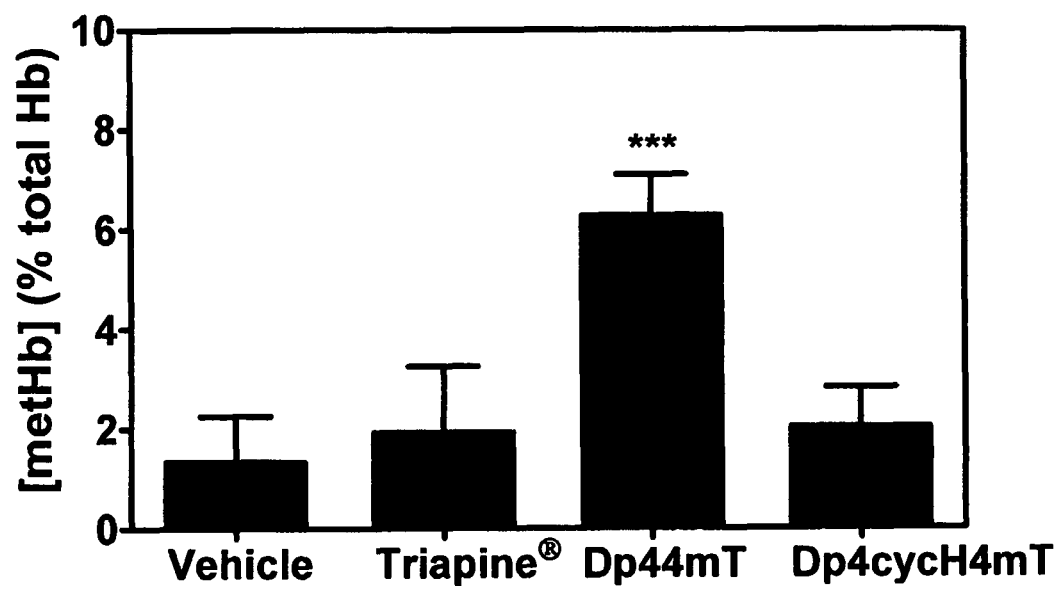
FIG. 13. Effect of thiosemicarbazone chelators on metHb-formation in vivo. MetHb after Dp44mT, Triapine® or Dp4cycH4mT treatment in vivo at a dose of 6 mg/kg administered intravenously via the tail vein. Mice in the control group were treated with vehicle alone. At 30 minutes post-administration, whole blood was collected for determination of metHb levels.

C57BL6 mice were administered Dp44mT (6 mg/kg), Triapine® (6 mg/kg) or Dp4cycH4mT (6 mg/kg) intravenously and blood taken after 30 min to assess metHb (FIG. 13). As previously observed, Dp44mT induced significant (p<0.001) levels of metHb relative to the vehicle (6.3±0.8 compared to 1.3±0.9% metHb % of total Hb respectively), while metHb levels induced by Dp4cycH4mT were comparable to the control (FIG. 13).

This result with Dp4cycH4mT confirmed the results of the in vitro studies in Example 5a and further suggests that Dp4cycH4mT may have the specific advantage of not inducing metHb compared to Dp44mT.

Example 5c

Figure 14:
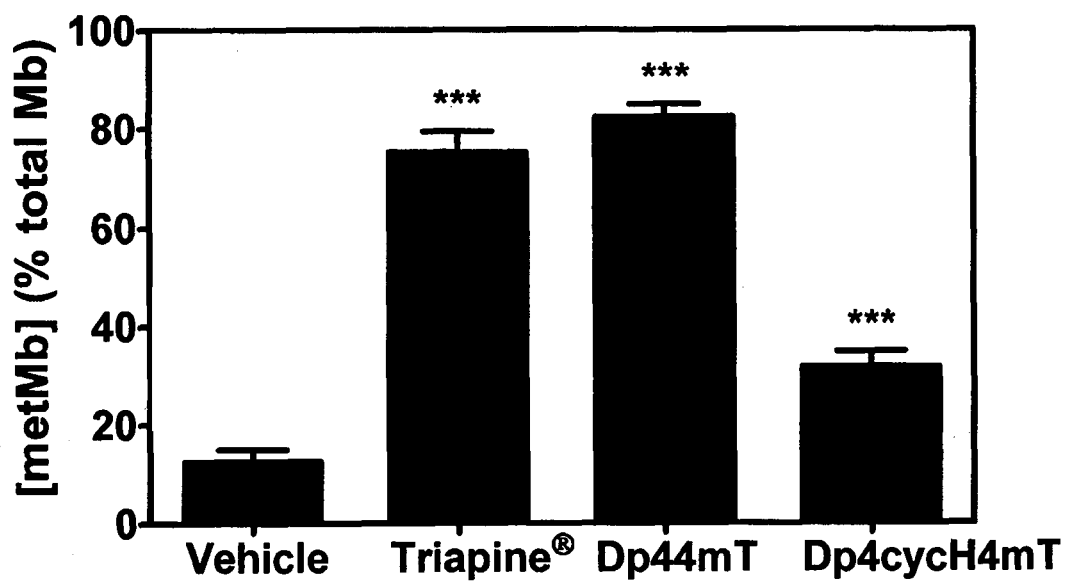
FIG. 14. Effect of thiosemicarbazone chelators on metMb-formation in vivo. MetMb levels after Dp44mT Triapine® or Dp4cycH4mT treatment in vivo at a dose of 6 mg/kg administered intravenously via the tail vein. Mice in the control group were treated with vehicle alone. At 30 min post-administration, whole hearts were collected for determination of metMb levels.

Ability of the Iron Chelators Triapine, Dp44mT and Dp4cycH4mT to Induce metmyoglobin (metMb) Formation in vivo The protein myoglobin (Mb) plays an important role in oxygen storage and donation to muscles and is a monomeric counterpart to hemoglobin. Accordingly, the effect of potent anticancer active chelators on metMb formation in vivo was assessed. C57BL6 mice were administered Dp44mT (6 mg/kg), Triapine® (6 mg/kg) or Dp4cycH4mT (6 mg/kg) intravenously and blood taken after 30 min to assess metMb (FIG. 14).

The chelator Dp44mT induced significant (p<0.001) levels of metMb (82.3±2.6%) which was similar to that of Triapine® (75.2±4.2%), whereas Dp4cycH4mT generated significantly (p<0.001) lower levels of metMb (31.7±3.2%; FIG. 14).

However, Dp4cycH4mT-mediated levels of metMb were significantly (p<0.001) higher than the control (12.6±2.4%; FIG. 14).

Collectively, the properties of Dp4cycH4mT, in terms of being significantly less effective at inducing metHb- and metMb-formation, while maintaining anti-tumor activity (Kovacevic Z, Chikhani S, et al., (2011). *Mol Pharm* 80: 598-609) suggest that Dp4cycH4mT has significant advantages over Triapine® and Dp44mT.

We claim:

1. A compound of general formula (I):

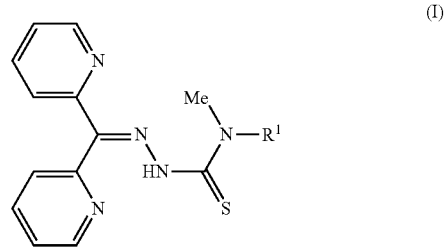

wherein $R^1$ is cyclohexyl or ethyl;
and salts, hydrates and solvates thereof.

2. The compound according to claim 1, which is di-2-pyridylketone 4-ethyl-4-methyl-3-thiosemicarbazone, and salts, hydrates and solvates thereof.

3. The compound according to claim 1, which is di-2-pyridylketone 4-cyclohexyl-4-methyl-3-thiosemicarbazone, and salts, hydrates and solvates thereof.

4. The compound according to claim 1, wherein the salts are pharmaceutically acceptable salts.

5. The compound according to claim 2, which is di-2-pyridylketone 4-ethyl-4-methyl-3-thiosemicarbazone hydrochloride.

6. The compound according to claim 3, which is di-2-pyridylketone 4-cyclohexyl-4-methyl-3-thiosemicarbazone hydrochloride.

7. A pharmaceutical composition comprising a compound of formula (I), or a salt, hydrate or solvate thereof according to claim 1, together with a pharmaceutically acceptable excipient, diluent or adjuvant.

8. A method of treating cancer in a mammal, wherein the cancer is selected from the group consisting of melanoma, skin cancer, breast cancer, prostate cancer, bladder cancer, liver cancer, gastrointestinal cancer, colon and rectal cancer, brain cancer, head and neck cancer, bone cancer, pancreatic cancer, uterine cancer, ovarian cancer, cervical cancer, lung cancer and haematological tumours, the method comprising administering to a mammal in need thereof an effective amount of a compound of formula (I), or a salt, hydrate or solvate thereof according to claim 1.

9. The method according to claim 8, wherein the cancer is selected from the group consisting of brain cancer, head and neck cancer, bone cancer, pancreatic cancer, uterine cancer, ovarian cancer, cervical cancer, lung cancer and haematological tumours.

10. The method according to claim 9, wherein the cancer is selected from the group consisting of pancreatic cancer, lung cancer and brain cancer.

11. The method according to claim 9, wherein the cancer is a solid tumour.

12. The method according to claim 8, wherein the mammal is a human.

13. A method of treating cancer in a mammal, wherein the cancer is selected from the group consisting of melanoma, skin cancer, breast cancer, prostate cancer, bladder cancer, liver cancer, gastrointestinal cancer, colon and rectal cancer, brain cancer, head and neck cancer, bone cancer, pancreatic cancer, uterine cancer, ovarian cancer, cervical cancer, lung cancer and haematological tumours, the method comprising administering to a mammal in need thereof an effective amount of a pharmaceutical composition according to claim 7.

\* \* \* \* \*